United States Patent
Nash et al.

[19]

[11] Patent Number: 6,017,352
[45] Date of Patent: Jan. 25, 2000

[54] SYSTEMS FOR INTRAVASCULAR PROCEDURES AND METHODS OF USE

[75] Inventors: John E. Nash; Douglas G. Evans, both of Downingtown, Pa.

[73] Assignee: Kensey Nash Corporation, Exton, Pa.

[21] Appl. No.: 09/008,266

[22] Filed: Jan. 16, 1998

Related U.S. Application Data

[63] Continuation-in-part of application No. 08/923,682, Sep. 4, 1997.

[51] Int. Cl.⁷ ..................................................... A61B 17/08
[52] U.S. Cl. ............................................................... 606/153
[58] Field of Search .................................... 606/153, 154, 606/151, 139, 152, 219; 623/1

[56] References Cited

U.S. PATENT DOCUMENTS

| | | |
|---|---|---|
| 2,127,903 | 8/1938 | Bowen . |
| 3,155,095 | 11/1964 | Brown . |
| 3,588,920 | 6/1971 | Wesolowski . |
| 3,620,218 | 11/1971 | Schmitt et al. . |
| 3,683,926 | 8/1972 | Suzuki . |
| 4,214,586 | 7/1980 | Mericle . |
| 4,233,981 | 11/1980 | Schomacher . |
| 4,352,358 | 10/1982 | Angelchik . |
| 4,366,819 | 1/1983 | Kaster ..................................... 606/153 |
| 4,368,736 | 1/1983 | Kaster ..................................... 606/153 |
| 4,470,415 | 9/1984 | Wozniak . |
| 4,501,263 | 2/1985 | Harbuck . |
| 4,512,761 | 4/1985 | Raible . |
| 4,523,592 | 6/1985 | Daniel . |
| 4,552,148 | 11/1985 | Hardy, Jr. et al. . |
| 4,553,542 | 11/1985 | Schenck et al. . |
| 4,577,631 | 3/1986 | Kreamer . |
| 4,657,019 | 4/1987 | Walsh et al. . |
| 4,675,008 | 6/1987 | Tretbar . |
| 4,721,109 | 1/1988 | Healey . |
| 4,753,236 | 6/1988 | Healey . |
| 4,769,029 | 9/1988 | Patel . |
| 4,816,028 | 3/1989 | Kapadia et al. . |
| 4,851,001 | 7/1989 | Taheri . |
| 4,854,318 | 8/1989 | Solem et al. . |
| 4,930,502 | 6/1990 | Chen . |
| 4,931,057 | 6/1990 | Cummings et al. . |
| 4,957,499 | 9/1990 | Lipatov et al. . |
| 5,123,908 | 6/1992 | Chen . |
| 5,156,619 | 10/1992 | Ehrenheld . |
| 5,192,289 | 3/1993 | Jessen . |
| 5,222,963 | 6/1993 | Brinkerhoff et al. . |
| 5,250,058 | 10/1993 | Miller et al. . |
| 5,250,060 | 10/1993 | Carbo et al. . |
| 5,330,490 | 7/1994 | Wilk et al. . |
| 5,346,501 | 9/1994 | Regula et al. . |
| 5,364,389 | 11/1994 | Anderson . |
| 5,395,311 | 3/1995 | Andrews . |
| 5,399,352 | 3/1995 | Hanson . |
| 5,425,738 | 6/1995 | Gustafson et al. . |
| 5,425,739 | 6/1995 | Jessen . |
| 5,443,497 | 8/1995 | Venbrux . |

(List continued on next page.)

*Primary Examiner*—Michael Buiz
*Assistant Examiner*—(Jackie) Tan-Uyen T. Ho
*Attorney, Agent, or Firm*—Caesar, Rivise, Bernstein, Cohen & Pokotilow, Ltd.

[57] ABSTRACT

A system and method of use for effecting the bypass or other anastomosis of a portion of a native blood vessel, duct, lumen or other tubular organ within the body of a living being. The system includes a connector assembly and a deployment instrument for carrying the device to the desired position within the vessel, duct, lumen or tubular organ. The system includes a piercerdilator instrument to form an opening in the wall of the vessel, duct, lumen or tubular organ into which the connector assembly is deployed by the deployment instrument. The connector assembly is at least partially formed of a resorbable material and includes movable members for securing it to the tissue of the vessel, duct, lumen or tubular organ contiguous with the opening. Other components may be included in the device for expediting the anastomosis procedure, with or without the use of sutures. Moreover, the system can be used to bypass of at least two coronary arteries by a common connection with the aorta utilizing at least two bypass grafts and plural connectors for securement to the aorta and the coronary arteries.

14 Claims, 12 Drawing Sheets

U.S. PATENT DOCUMENTS

| | | |
|---|---|---|
| 5,445,644 | 8/1995 | Pietrafitta et al. . |
| 5,447,514 | 9/1995 | Gerry et al. . |
| 5,456,712 | 10/1995 | Maginot . |
| 5,456,714 | 10/1995 | Owen . |
| 5,503,635 | 4/1996 | Sauer et al. . |
| 5,509,902 | 4/1996 | Raulerson . |
| 5,571,167 | 11/1996 | Maginot ..................... 623/1 |
| 5,586,987 | 12/1996 | Fahy . |
| 5,591,226 | 1/1997 | Trerotola et al. . |
| 5,676,670 | 10/1997 | Kim . |
| 5,695,504 | 12/1997 | Gifford, III et al. ............ 606/153 |
| 5,709,335 | 1/1998 | Heck . |
| 5,727,569 | 3/1998 | Benetti et al. . |

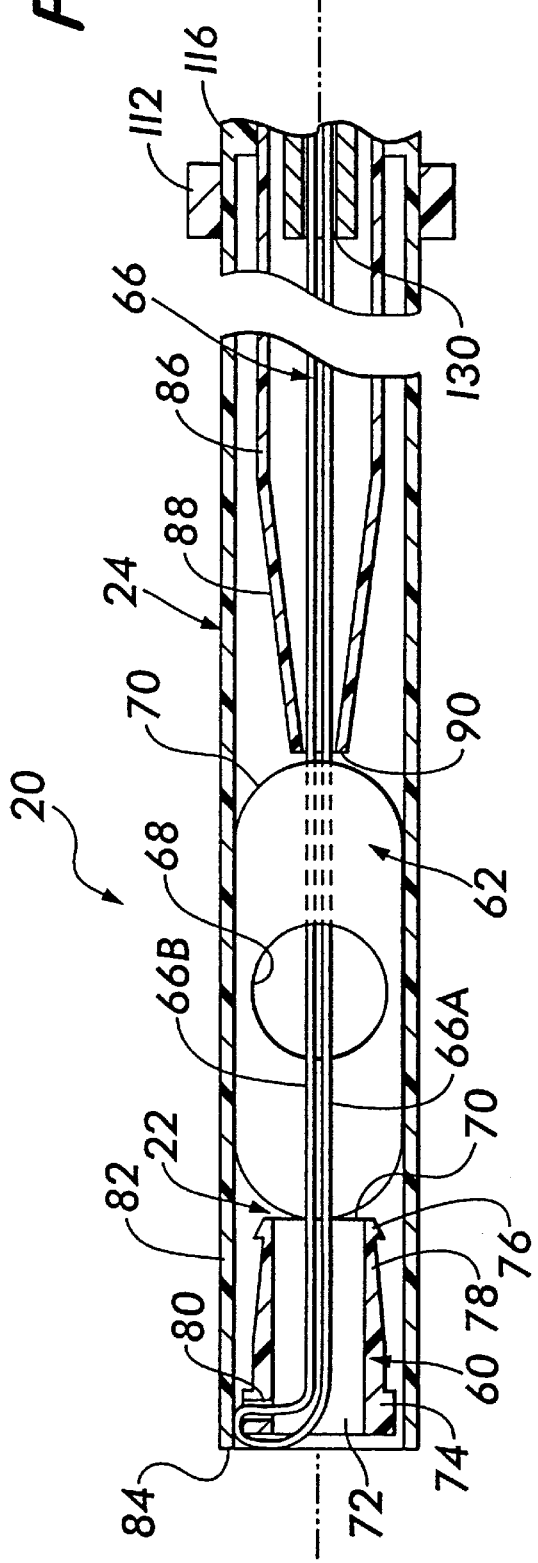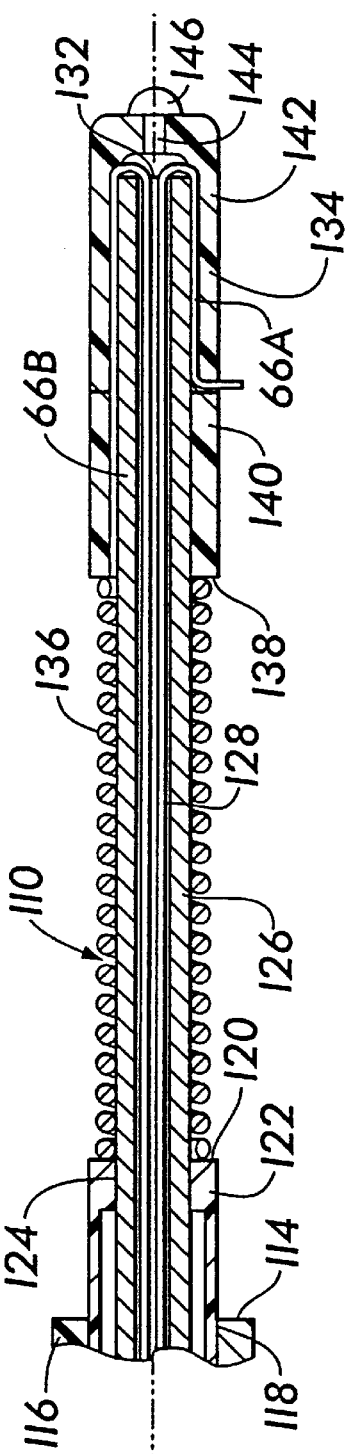
FIG.1

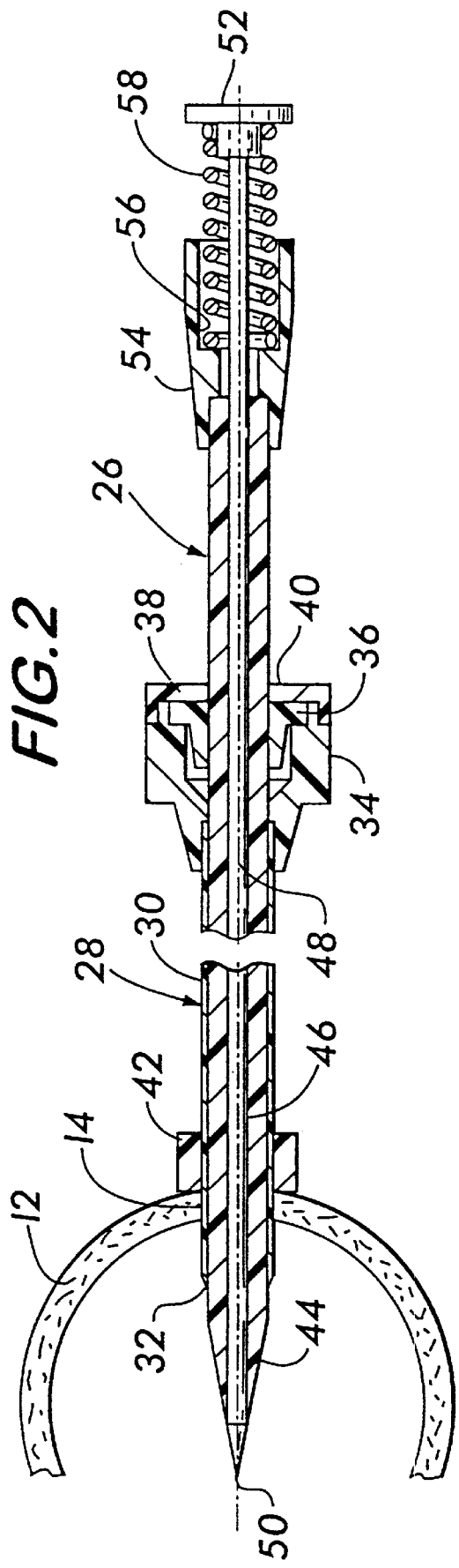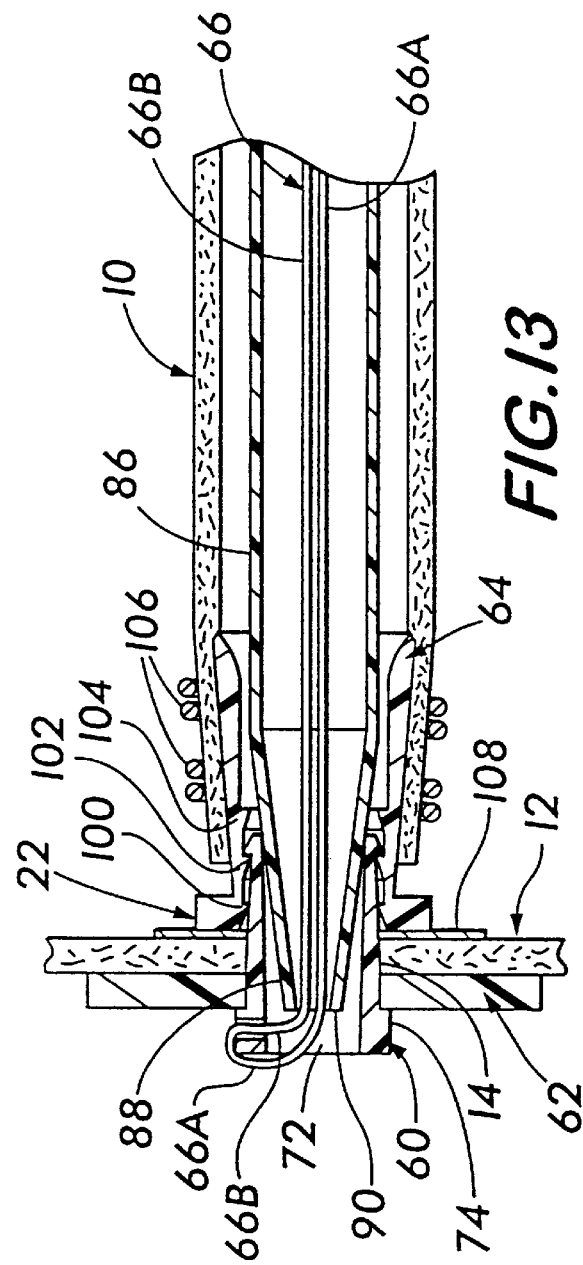

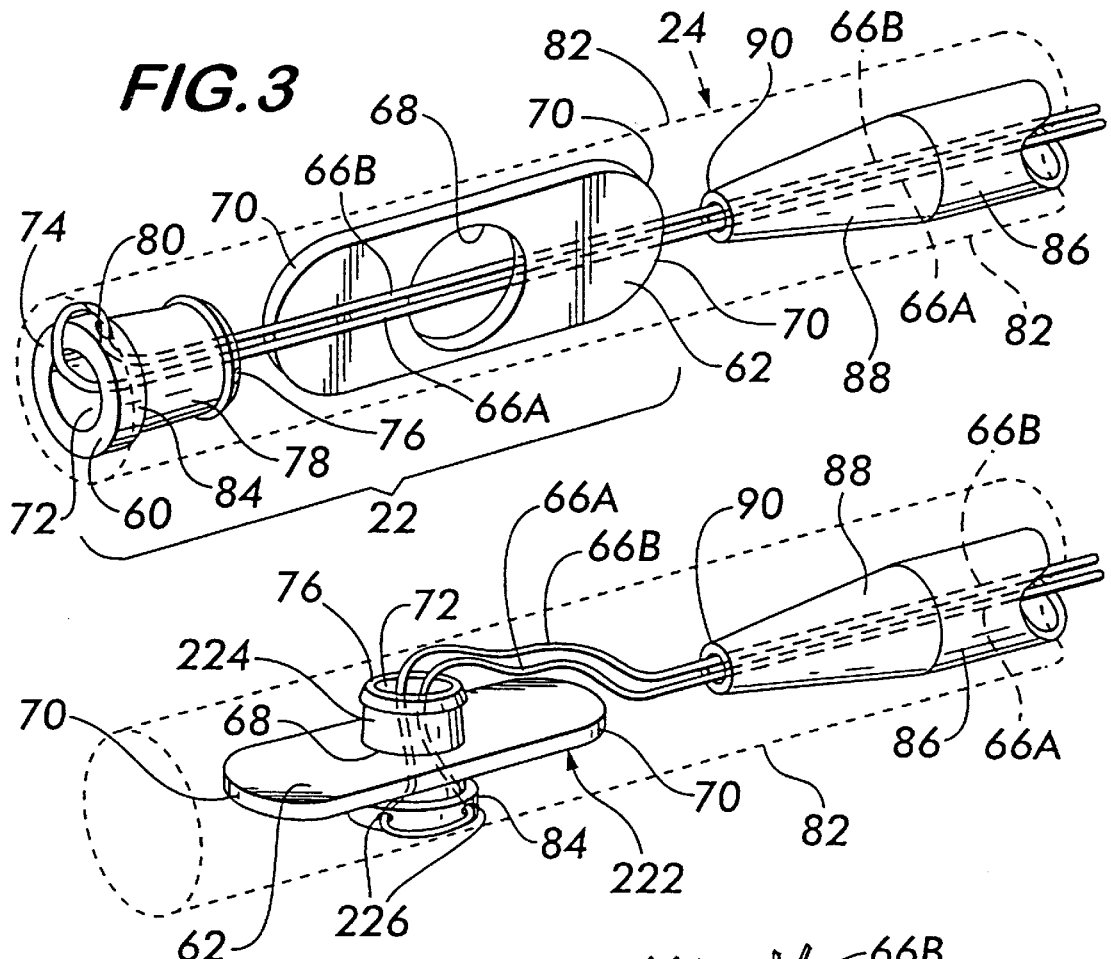
FIG.3
FIG.4
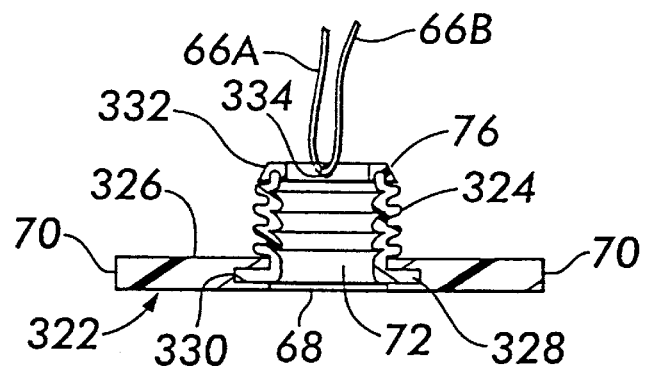
FIG.5
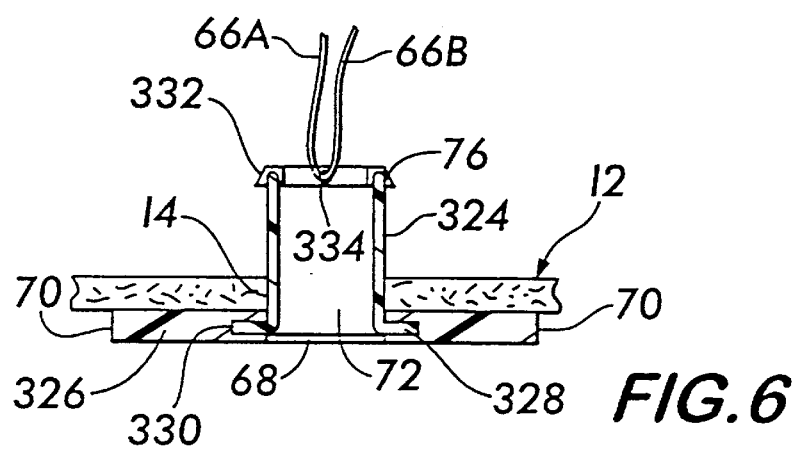
FIG.6

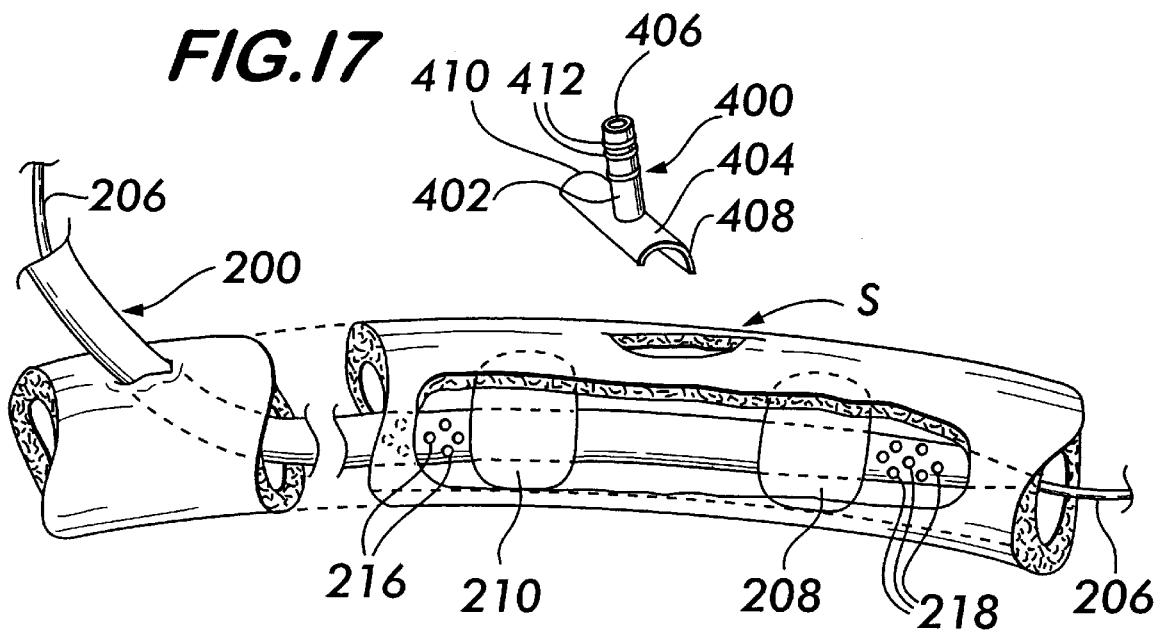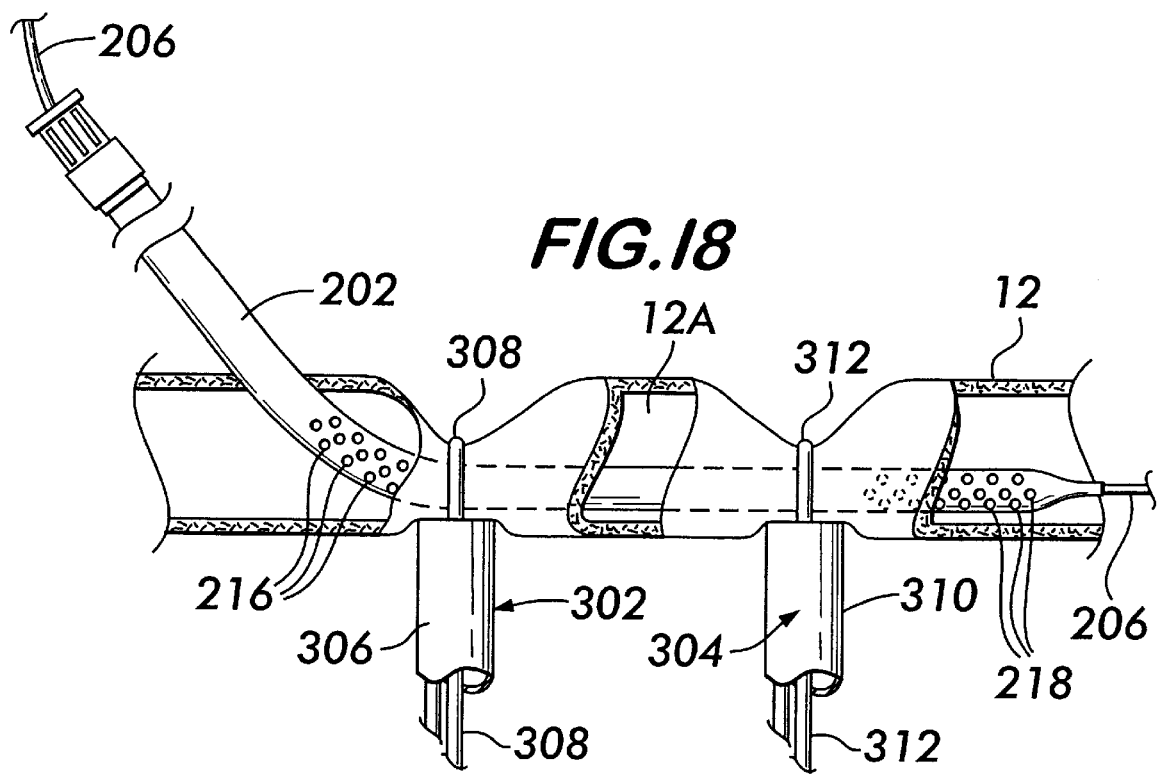

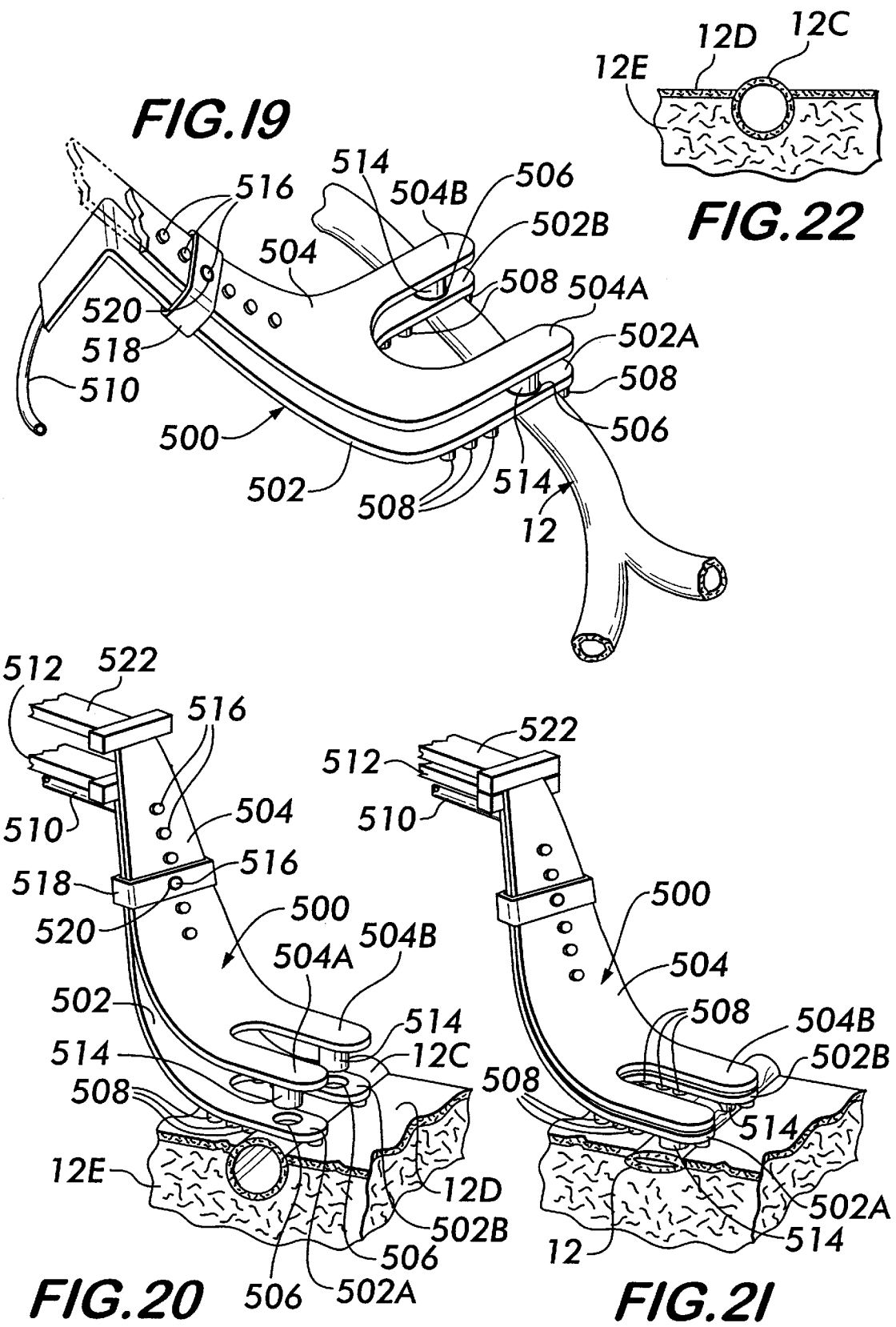

SYSTEMS FOR INTRAVASCULAR PROCEDURES AND METHODS OF USE

This application is a Continuation-In-Part of our earlier application Ser. No. 08/923,682, filed on Sep. 4, 1997, entitled Connector System For Vessels, Ducts, Lumens Or Hollow Organs And Methods Of Use (hereinafter the "'682 application"), which is assigned to the same assignee as this invention and whose disclosure is incorporated by reference herein.

BACKGROUND OF THE INVENTION

This invention relates generally to medical devices and methods of performing surgical procedures and more particularly to the anastomosis of blood vessels, ducts, lumens or other tubular organs or other surgical procedures involving such structures.

Arterial bypass surgery is a common modality for the treatment of occlusive vascular disease. Such surgery typically involves a formal surgical incision and exposure of the occluded vessel followed by the joinder of a graft, e.g., a mammary artery, saphenous vein, or synthetic graft (all collectively referred to hereinafter as the "bypass graft"), to the occluded vessel (hereinafter the "native" blood vessel) distally (downstream) of the occlusion. The upstream or proximal end of the bypass graft is secured to a suitable blood vessel upstream of the occlusion, e.g., the aorta, to divert the flow of blood around the blockage. Other occluded or diseased blood vessels, such as the carotid artery, may be similarly treated. Moreover, similar procedures are conducted to place a graft between an artery and a vein in dialysis patients.

While such surgical procedures are widely practiced they have certain inherent operative limitations. For example, sewing the graft to the host vessel, known as anastomosis, requires complex and delicate surgical techniques to accomplish the optimum result. Various complications must be avoided when anastomosing a bypass graft, whether it be a natural graft or a synthetic graft. For example, it is important that the juncture between the native vessel and the bypass graft form a smooth uniform transition without narrowing or regional irregularities which could tend to reduce blood flow. Moreover, any protuberances into the lumen could obstruct blood flow and may produce turbulence, thereby increasing the risk of clotting and/or restenosis. In addition, the difference in size between the typically larger internal diameter of the bypass graft and the typically smaller native artery may also produce unwanted turbulence in the blood. All of these characteristics can greatly diminish the effectiveness and patency of the graft.

Various devices and methods of use have been disclosed for effecting anastomosis of blood or other vessels, ducts, lumens or other tubular organs. Examples of such devices and methods are found in U.S. Pat. No. 2,127,903 (Bowen), U.S. Pat. No. 3,155,095 (Brown), U.S. Pat. No. 3,588,920 (Wesolowski), U.S. Pat. No. 3,620,218 (Schmitt et al.), U.S. Pat. No. 3,683,926 (Suzuki), U.S. Pat. No. 4,214,586 (Mericle), U.S. Pat. No. 4,233,981 (Schomacher), U.S. Pat. No. 4,366,819 (Kaster), U.S. Pat. No. 4,368,736 (Kaster), U.S. Pat. No. 4,470,415 (Wozniak), U.S. Pat. No. 4,501,263 (Harbuck), U.S. Pat. No. 4,675,008 (Tretbar), U.S. Pat. No. 4,512,761 (Raible), 4,552,148 (Hardy, Jr. et al.), U.S. Pat. No. 4,721,109 (Healy), U.S. Pat. No. 4,753,236 (Healy), U.S. Pat. No. 4,769,029 (Patel), U.S. Pat. No. 4,851,001 (Taheri), U.S. Pat. No. 4,816,028 (Kapadia et al.), U.S. Pat. No. 4,854,318 (Solem et al.), U.S. Pat. No. 4,930,502 (Chen), U.S. Pat. No. 4,931,057 (Cummings et al.), U.S. Pat. No. 4,957,499 (Lipatov et al.), U.S. Pat. No. 5,156,619 (Ehrenfeld), U.S. Pat. No. 5,123,908 (Chen), U.S. Pat. No. 5,192,289 (Jessen), U.S. Pat. No. 5,250,058 (Miller), U.S. Pat. No. 5,222,963 (Brinkerhoff et al.), U.S. Pat. No. 5,330,490 (Wilk et al.), U.S. Pat. No. 5,346,501 (Regula et al.), U.S. Pat. No. 5,364,389 (Anderson), U.S. Pat. No. 5,399,352 (Hanson), U.S. Pat. No. 5,425,738 (Gustafson et al.), U.S. Pat. No. 5,425,739 (Jessen), U.S. Pat. No. 5,443,497 (Venbrux), U.S. Pat. No. 5,445,644 (Pietrafitta et al.), U.S. Pat. No. 5,447,514 (Gerry et al.), U.S. Pat. No. 5,456,712 (Maginot), U.S. Pat. No. 5,456,714 (Owen), U.S. Pat. No. 5,503,635 (Sauer et al.), U.S. Pat. No. 5,509,902 (Raulerson), U.S. Pat. No. 5,571,167 (Maginot), U.S. Pat. No. 5,586,987 (Fahy) and U.S. Pat. No. 5,591,226 (Trerotola et al.).

In our copending U.S. patent application Ser. No. 08/861,584 filed on May 22, 1997 entitled Anastomosis System And Method of Use (hereinafter the "'584 application"), which is assigned to the same assignee as this invention and whose disclosure is incorporated by reference herein, there is disclosed and claimed anastomosis systems and methods of use which overcome many of the disadvantages of the prior art.

Notwithstanding the inventions of our aforementioned '684 and '584 applications, it is perceived that further improvements to systems for forming an anastomosis connection within the body of a living being are desirable and/or needed.

OBJECTS OF THE INVENTION

It is a general object of this invention to provide a system and method of use which addresses that desire/need.

It is a further object of this invention to provide a system and method of use for quickly, easily and safely effecting the anastomosis of a bypass graft to a native blood vessel.

SUMMARY OF THE INVENTION

These and other objects of the instant invention are achieved by providing a system for forming an anastomosis junction of a first vessel, duct, lumen or hollow organ, e.g., a coronary bypass graft, to a native vessel, duct, lumen or hollow organ, e.g., the aorta, of a living being at an anastomosis site. The system basically comprises an anastomosis connector and fluid flow preclusion means. The anastomosis connector is arranged for securement to the native vessel, duct, lumen or hollow organ and to the first vessel, duct, lumen or hollow organ so that they are in fluid communication with each other, e.g., so that blood can flow from the aorta through the bypass graft to a downstream connection of an occluded coronary artery. The fluid flow preclusion means, e.g., a tubular member having a passageway and a pair of spaced apart expandable balloons, is arranged for insertion within the body of the being. The fluid flow preclusion means is operative, e.g., the balloons inflated, during the securement of the anastomosis connector to the vessels, ducts, lumens or hollow organs to form a zone, e.g., the space between the two balloons, contiguous with the anastomosis site through which fluid, e.g., blood, is temporarily precluded from flowing to facilitate the formation of the anastomosis junction.

In accordance with one preferred aspect of this invention blood is enabled to flow through the passageway in the tubular member to perfuse downstream vessels while the fluid flow preclusion means, e.g., the two balloons, form the zone through which fluid, e.g, blood, is precluded to flow.

DESCRIPTION OF THE DRAWING

Other objects and many of the attendant advantages of this invention will become readily appreciated as the same becomes better understood by reference to the following detailed description when considered in connection with the accompanying drawing wherein:

FIG. 1 is a longitudinal sectional view of one embodiment of a first connector assembly and a deployment instrument which form a portion of the connector system of this invention for creating a fluid access port in a vessel, duct, lumen or tubular organ or for effecting the anastomosis between two vessels, ducts, lumens or tubular organs within the body of a living being;

FIG. 2 is a longitudinal sectional view of a piercing instrument and an introducer sheath also forming a portion of the connector system of this invention shown during the process of forming a small opening in the wall of the vessel, duct, lumen or tubular organ;

FIG. 3 is an enlarged, isometric view of the embodiment of the connector assembly of FIG. 1 shown in its "stowed" state disposed within the deployment instrument of this invention prior to its deployment;

FIG. 4 is an enlarged isometric view, similar to FIG. 3, but showing another embodiment of a connector assembly constructed in accordance with this invention and shown in its "stowed" state prior to its deployment;

FIG. 5 is a longitudinal sectional view showing yet another embodiment of a connector assembly constructed in accordance with this invention shown in its compact or "stowed" state prior to its deployment;

FIG. 6 is a longitudinal sectional view, similar to FIG. 5, but showing the embodiment thereof in its deployed state extending through an opening in the wall of a vessel, duct, lumen or tubular organ;

FIG. 13 is an enlarged longitudinal sectional view of the distal end of the deployment instrument of FIG. 12 during the anastomosis connecting procedure;

FIG. 17 is a view similar to FIG. 16 but showing the isolation instrument during the formation of an anastomosis connection utilizing an embodiment of the anastomosis connector of the '584 application;

FIG. 18 is a longitudinal sectional view similar to FIG. 15 but showing an alternative isolation instrument of this invention for location within a vessel, duct, lumen or hollow organ to temporarily preclude blood or other fluid from flowing therethrough to facilitate the formation of an anastomosis connection or to accomplish some other procedure on the wall of thereof;

FIG. 19 is an isometric view of another alternative embodiment of an isolation instrument of this invention showing its operation at an early step in the process of isolating a portion of a blood vessel, e.g., a coronary artery, to preclude the flow of blood therethrough to enable some procedure, e.g., an anastomosis, to be accomplished on wall of that vessel;

FIG. 20 is an isometric view of the isolation instrument of FIG. 19 shown at an initial step in the process of isolating the vessel section so that an anastomosis can be accomplished thereat;

FIG. 21 is a view similar to FIG. 20, but showing the instrument at a later step in that process;

FIG. 22 is an enlarged sectional view of a portion of the heart showing a coronary artery located in the epicardium prior to use of the isolation instrument of FIG. 22 (or of any other isolation instrument constructed in accordance with this invention);

DETAILED DESCRIPTION OF PREFERRED EMBODIMENTS

Figure 7:
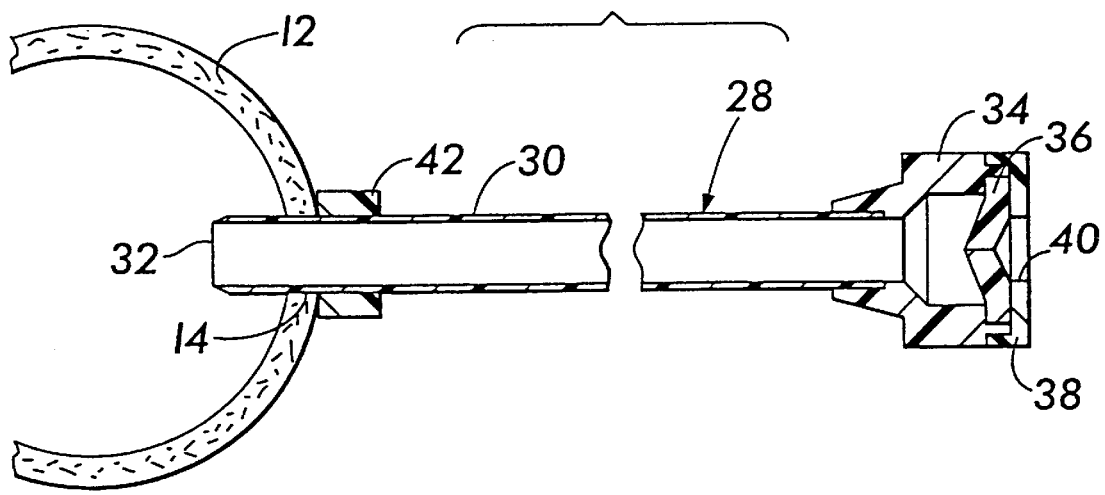
FIG. 7 is a longitudinal sectional view of the introducer sheath shown in FIG. 2 extending into an opening formed within a vessel, duct, lumen or tubular organ.

Referring now to the drawing wherein like reference characters refer to like parts, there is shown at 20 in FIG. 1 an connector system constructed in accordance with the subject invention.

Referring now to the various figures of the drawing wherein like reference characters refer to like parts, there is shown at 20 in FIG. 1 a connector system constructed in accordance with the subject invention. The system can be used to effect the anastomosis of any two vessels, ducts, lumens or tubular organs. In fact, the system 20 can be used to form a fluid access port in any vessel, duct, lumen or tubular organ.

Figure 14:
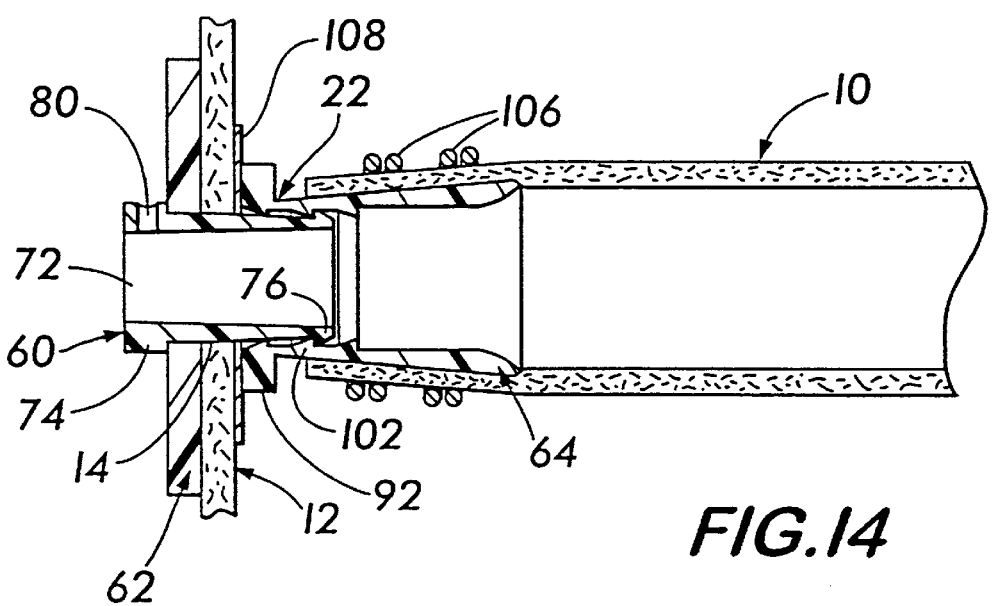
FIG. 14 is a longitudinal sectional view showing the completed anastomotic connection between the two vessel, ducts, lumens or tubular organs.

One particularly useful anastomosis application of the subject system is for effecting the bypass of an occluded coronary artery. This may be accomplished by forming an anastomotic connection between a saphenous vein graft and the aorta upstream of the occluded coronary artery. The completed anastomotic connection between the bypass graft and the aorta is shown in FIG. 14, wherein the bypass graft is designated by the reference numeral 10 and the aorta by the reference numeral 12.

The system basically comprises a first connector assembly 22 (FIGS. 1 and 14), a deployment instrument 24 (FIGS. 1 and 12), a piercer-dilator instrument 26 (FIG. 2) and an introducer sheath 28 (FIGS. 2 and 7). The deployment instrument 24 will be described in considerable detail later. Suffice it for now to state that the instrument 24 is arranged to house a portion of the connector assembly 22 therein and to deploy it within an opening formed in the wall of the vessel, duct, lumen or tubular organ so that a fluid access port or an anastomosis connection can be completed. As will also be described later, the deployment instrument 24 is arranged to be used after the piercer-dilator instrument (or some other means not shown) has formed a small opening 14 (FIG. 2) in the wall of the vessel, duct, lumen or tubular organ 12 to which the fluid access port or anastomosis connection is to be made and the introducer sheath 28 has been located within that opening.

Before describing the details of the piercer-dilator instrument 26, a brief description of the introducer sheath 28 is in order. To that end, as can be seen best in FIG. 7, the introducer sheath is of generally conventional construction and includes an elongated tubular body 30, e.g., an 8–14 French tube. The tubular body is formed of a biocompatible material, such as plastic, and has an open distal end 32 and closed proximal end 34. The proximal end 34 is closed by means of a conventional hemostasis valve housing including a resilient valve member 36 disposed therein. A sealing cap 38 holds the valve member 36 in place and includes a central opening 40 through which any suitable elongated member or instrument can be passed through the valve member 36 and the associated tube 30. As will be described hereinafter the piercer-dilator 26 is extended through the introducer sheath 28 and those two devices are used together to form the small opening 14 in the vessel, duct, lumen or tubular organ. Once the opening 14 has been formed, the piercer-dilator is removed from the sheath 28 and the introducer instrument 24 with the connection assembly 22 therein is passed through the introducer sheath to deploy the connector assembly. In order to prevent excessive penetration of the piercer-dilator into the vessel, duct, lumen or tubular organ during the formation of the opening 14 in the wall thereof, the introducer sheath 28 includes an annular stop 42 closely adjacent its open distal end 32.

Turning now to FIG. 2, the details of piercer-dilator 26 will now be described. Thus, as can be seen therein, the piercer-dilator 26 basically comprises an elongated tubular body having a tapered distal end 44. A central passageway 46 extends down the entire length of the body 44. A needle-plunger 48 extends through the passageway and terminates at its distal end in a sharply pointed tip 50. The proximal end of the needle-plunger is in the form of an enlarged head or cap 52. A cup shaped member 54 is mounted on the proximal end of the tubular body 44 of the piercerdilator 26. The cup shaped member 54 includes central bore recess 56 arranged to receive one end of a helical compression spring 58. The other end of the helical spring engages the under surface of the cap 52. The spring is normally in its uncompressed state. It is shown in FIG. 2 in its compressed state, i.e., the state wherein the plunger cap 52 is pressed in the distal direction with respect to the cup shaped member 54. This action causes the piercing point 50 of the plunger to extend out of the opening at the tapered distal end of the dilator body 44. It is in this condition that the piercer-dilator is used to form the small opening 14 in the wall of the vessel, duct, lumen or tubular organ to which the access port or anastomosis connection is to be made. To that end, the piercer-dilator 26 is introduced through the hemostasis valve in the introducer sheath 28 until its distal end extends slightly beyond the open free end 32 of the sheath 28. A stop (not shown) is provided to ensure that the tip of the needle-dilator body does not extend too far beyond the open end of the sheath. With the needle-dilator in place the plunger cap 52 is pressed, i.e., moved distally with respect to the body of the piercer-dilator, whereupon the piercing point 50 extends out of the piercer-dilator. The exposed pointed tip 50 of the piercer-dilator instrument is then brought into engagement with the outer surface of the vessel, duct, lumen or tubular body, e.g., the aorta 12, at which the opening 14 is to be formed. The introducer sheath and the piercer-dilator are then pushed distally in through the wall of the vessel, duct, lumen or tubular organ, whereupon a small opening is formed. Further pushing of the needle-dilator into the opening enlarges it as the flared conical surface of the distal free end of the dilator body 44. Further pushing in the distal direction on the piercer-dilator instrument 26 and the introducer sheath 28 as a unit causes the distal end of the introducer sheath to enter into the opening 14. The combined piercer-dilator instrument and the introducer sheath are pushed inward until the stop 42 engages the outer surface of the wall of the vessel, duct, lumen or tubular organ. At this point, no further penetration can be made. Thus, the stop prevents the piercing tip from engaging the wall of the vessel, duct or lumen opposite the opening 14. Once the opening has been formed, the piercer-dilator 26 can then be removed by retracting or pulling on it proximally to withdraw it out of the introducer sheath 28 while leaving the introducer sheath in place, such as shown in FIG. 7. The system 20 is now ready for the use of the deployment instrument 24 to deploy the connector assembly 22 through the opening 14 into the interior of the vessel, duct, lumen or tubular organ.

Before describing the details of the deployment instrument 24, a description of the connector assembly 22 is in order given. To that end, as can be seen clearly in FIGS. 1, 3, 9 and 11, the connector assembly 22 basically comprises a first connector member 60, an anchor member 62 and a second connector member. The first connector member and the anchor member are arranged to be deployed within the interior of the vessel, duct or lumen and then to be moved with respect to each other to assemble them in a manner whereupon the anchor member engages the interior of the vessel, duct, lumen or tubular organ contiguous with the opening 14 and a portion of the first connector member extends out through the opening 14 to provide a fluid access port or a connection point for the second connector member 64. In some applications, the first connector member and the anchor member can be used in and of themselves to form a fluid access port to the interior of the vessel, duct, lumen or tubular organ.

As can be seen clearly in FIG. 3, the first connector member 60 and the anchor member 62 are coupled together by a positioning member, e.g., a flexible filament 66. The filament is preferably in the form of a conventional resorbable monofilament suture (or if desired a non-resorbable suture).

The anchor member 62 is an elongated strip formed of a resorbable, somewhat rigid material, such as polyglactide, polyglycolide or copolymers thereof Non-absorbable materials, e.g., stainless steel, can be used for the anchor member. Each end of the anchor member 62 is rounded at 70. The first connector member 60 basically comprises a tubular body, preferably formed of the same material as that forming the anchor 62, and having a central passageway 72 extending therethrough. One end of the tube 74 is in the form of an annular flange. The flange need not be annular, and thus may merely be a tab or projection. The other end of the tube is in the form of at least one undercut annular lip or detent 76 whose exterior surface is chamfered. The outer surface 78 of the tubular connector body 60 between the flange 74 and the detent 76 is somewhat conical, i.e., is in the form of a surface which tapers from the flange 74 to the detent 76. The maximum outer diameter of the detent 76 of the connector member 60 is just slightly larger than the inside diameter of the hole 68 in the anchor member 62. A small aperture 80 extends radially outward from the central passageway 72 of the first connector member 60 through the annular flange 74.

As best seen in FIGS. 1 and 3, the filament 66 includes a pair of sequentially located sections 66A and 66B. In particular, section 66A extends from the proximal end of the deployment instrument 24 down the interior of that instrument through the central opening 68 in the anchor member 60, through the central passage 72 in the first connector member 60 from whence it doubles back to merge with the filament section 66B. The section 66B extends through the aperture 80 back into the interior passageway 72 in the first connector member 60 and through the central opening 68 in the anchor member 62. From there the section 66B of the filament 66 extends in the proximal direction through the deployment instrument to the proximal end thereof.

As mentioned earlier, the details of the deployment instrument will be described later, suffice it for now to state that this instrument includes a carrier 82 in the form of a tubular body in which the anchor member 62 and the first connector member 60 of the connector assembly 22 are disposed. The carrier tube includes an open, free (distal) end 84. As can be seen in FIGS. 1 and 3, the first connector member 60 is disposed within the carrier tube 82 immediately adjacent the open distal end 84, while the anchor member 62 is disposed immediately proximally of the first connector member.

The deployment instrument 24 also includes a guide-pusher assembly located within the carrier tube. The guide pusher assembly includes a tubular guide-pusher member 86 having a conical distal portion end 88. The free end 90 of the guide-pusher member includes a small opening communicating with the hollow interior of the guide-pusher and through which the filament sections 66A and 66B extend. The end 90 of the pusher member 86 is located immediately adjacent the proximally located rounded distal end 70 of the anchor member 62, when the anchor member is within the carrier tube in place as shown in FIGS. 1 and 3.

Deployment of the first connector member 60 and anchor member 62 is accomplished by operating the guide-pusher assembly, as will be described later, to cause the guide-pusher member 86 to push on the proximal end portion 70 of the anchor member 62 which in turn pushes on the distally located connector member 60 to expel the first connector member 60 out of the open free end 84 of the carrier member and out of the open end 32 of the introducer sheath 28 into the interior of the vessel, duct, lumen or tubular organ. Continued pushing on the guide pusher 86 in the distal direction then ejects the anchor member 62 into the interior of the vessel, duct, lumen or tubular organ.

Figure 9:
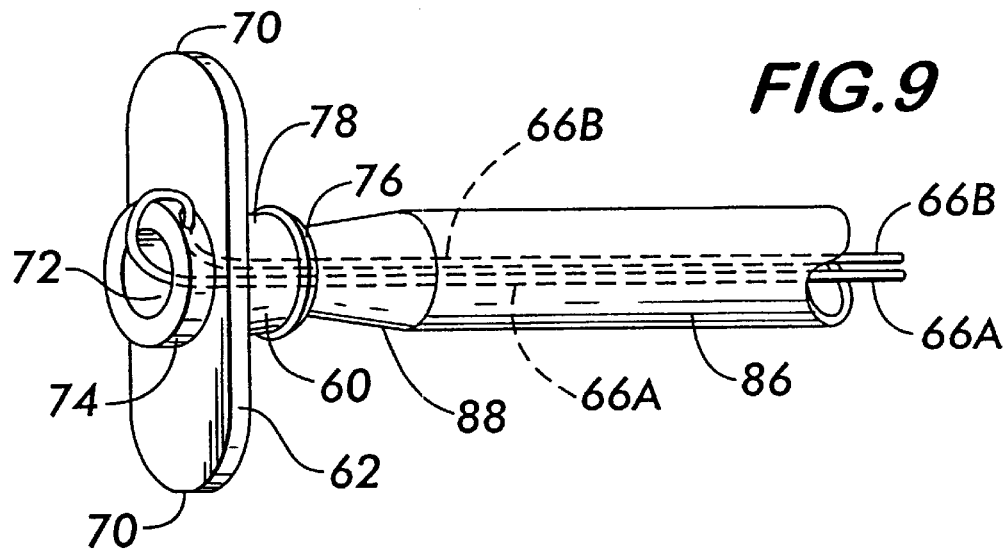
FIG. 9 is an isometric view of the connector assembly of FIG. 1, shown being assembled in its "deployed" state.
Figure 10:
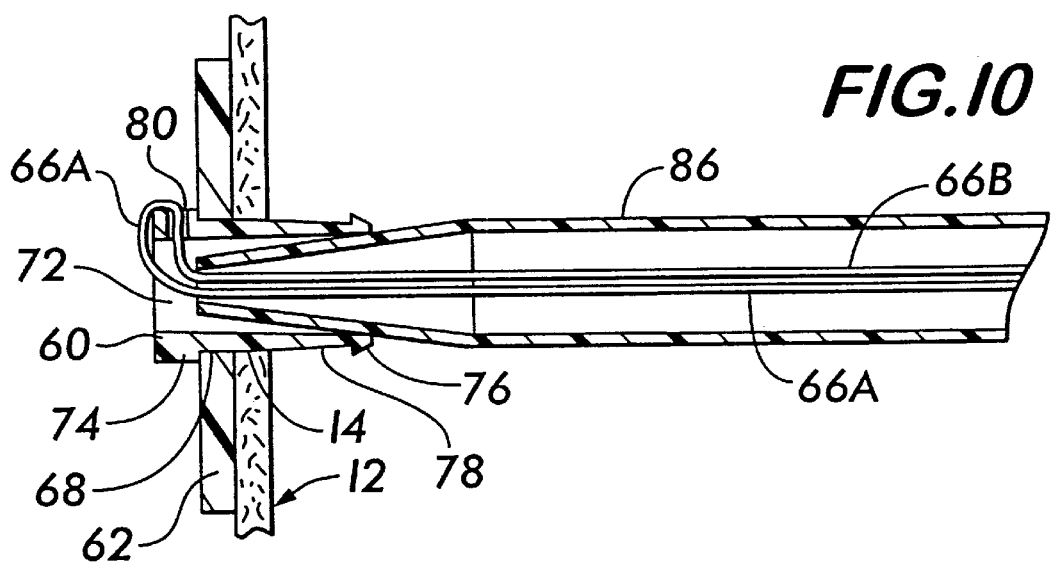
FIG. 10 is a longitudinal sectional view of the connector assembly of FIG. 1 shown during the deployment thereof in the opening in the wall of the vessel, duct, lumen or tubular organ.

In order to assemble the first connector member and anchor member and cause the detent end of the first connector member to be extended through the opening 14 in the wall of the vessel, duct, lumen or tubular organ, the two extending sections 66A and 66B of the filament 66 are retracted in the proximal direction, by means forming a portion of the instrument 24 to be described later. In particular, this retraction action on the filament sections pulls the first connector member toward the anchor member, whereupon the chamfered surface 76 of the first connector member enters into the central opening 68 in the anchor member. Continued retraction on the filament causes the anchor member to engage the interior surface of the vessel, duct, lumen or tubular organ contiguous with the opening 14 with the central opening 68 in the anchor member overlying the opening 14. Continued retraction of the two filament sections pulls the first connector member further into the central opening 68 in the anchor member, whereupon the portions of the anchor member contiguous with the central opening ride up the surface 78 of the first connector member until the flange 74 of the first connector member abuts the distally directed top surface of the anchor member 62, as shown in FIGS. 9 and 10. The retraction of the first connector member through the central opening 68 in the anchor member 62 causes the chamfered proximal end of the first connector member to pass through the opening 14 in the wall of the vessel, duct, lumen or tubular organ 12, as shown in FIG. 10. During the retraction of the filament sections 66A and 66B, the guide-pusher member 86 remains stationary so that its tapered distal end 88 enters into the central passageway 72 of the first connector member 60 when the first connector member is pulled through the opening 14 in the wall of the vessel, duct, lumen or tubular organ. Thus, the tapered end of the guide-pusher member 86 serves to guide or orient the first connector member 60 so that its central longitudinal axis is disposed generally perpendicularly to the wall of the vessel, duct, lumen or tubular organ 12, as shown in FIG. 10.

Figure 11:
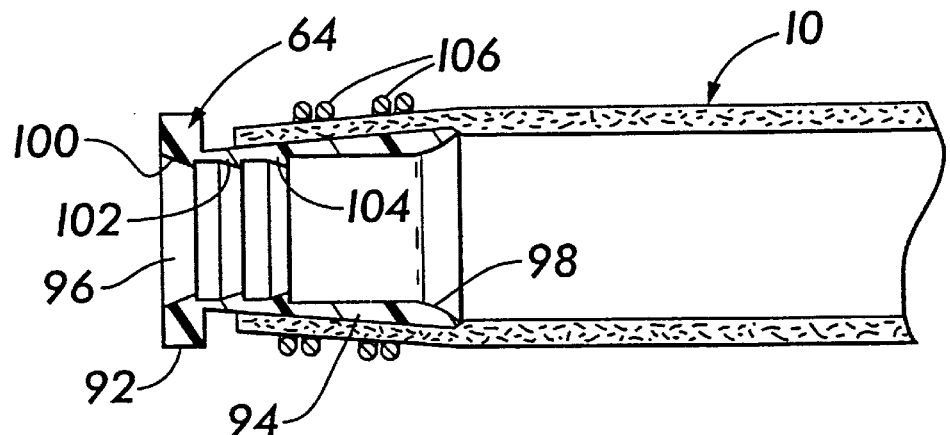
FIG. 11 is a longitudinal sectional view of another connector component forming another portion of the connector assembly of FIG. 1 and with a second vessel, duct, lumen or tubular organ secured thereto for forming an anastomotic connection between the two vessels, ducts, lumens or tubular organs.

With the first connector member 60 and the anchor member 62 deployed as shown in FIG. 10, the system is now ready to complete the anastomosis. To that end, the second connector member 64 is pre-mounted on the distal end of any desired vessel, duct, lumen or tubular organ like that shown in FIG. 11. For example, as shown in FIG. 11, the connector 64 can be disposed and secured within the open distal end of a saphenous vein bypass graft 10. The second connector member basically comprises a hollow tubular member, formed of the same material as that of the first connector 60 and the anchor member 62. The distal end of the second connector 64 is in the form of an annular flange 92. The outer surface of the tubular connector 64 proximally of the flange 92 is in the form of a slightly outwardly tapering conical surface 94, i.e., a surface whose diameter increases linearly in the proximal direction. A central passageway 96 extends through the length of the connector member 64, the proximal end of the passageway 96 forms a flared throat 98. Three annular undercut detent rings 100, 102 and 104 extend about the inter-periphery of the central passageway 96 at closely spaced locations adjacent the flanged distal end 92 of the connector 64. The outer surface of each of these detents is chamfered and is arranged to cooperate and engage the chamfered surface of the detent 76 of the first connector member 60 to lock the two connector members together, as will be described later. The flared proximal end of the second connector 64 is located within the hollow interior lumen of the bypass graft 10 and is secured in place therein by plural stainless steel springs 106. The springs extend about the periphery of the bypass graft to interpose that portion of the bypass graft tightly between the springs and the exterior surface 94 of the second connector member 64. Thus, the second connector member is fixedly secured to the distal end of the bypass graft.

The bypass graft with the second connector member fixedly secured thereto as shown in FIG. 11 is arranged to be deployed or slid down over the deployment instrument 24, as will be described later, and over the guide-pusher member 86 like shown in FIG. 13, whereupon the flange 92 of the second connector member 64 abuts the exterior surface of the vessel, duct, lumen or tubular organ contiguous with the opening 14 therein. The undercut surface of the detent surface 76 of the first connector member engages one of the undercut surfaces of the three chamfered detent rings 100, 102 or 104, with the particular detent being engaged being dependent upon the thickness of the wall of the vessel, duct, lumen or tubular organ.

In the embodiment shown in FIG. 13, the undercut portion of the detent 76 of the first connector member 60 engages the undercut portion of the detent ring 102 of the second connector member 64. This action effectively sandwiches the wall of the vessel, duct, lumen or tubular organ between the flange 92 of the second connector member 64 and the anchor member 62, thereby fixedly securing the connector assembly 22 in place within the opening 14, thereby completing the anastomosis.

In accordance with a preferred embodiment of this invention, a washer 108 is interposed between the flange 92 of the second connector member 64 and the outer surface of the wall of the vessel, duct, lumen or tubular organ contiguous with the opening 14 to prevent bleeding at the interface of the connector assembly and the opening 14 in the wall of the vessel, duct, lumen or tubular organ. The washer is preferably formed of a hemostatic material, e.g., collagen.

As should be appreciated from the previous discussion, the embodiment of the connector assembly 22 described heretofore makes use of components which are coupled together, but not assembled. By that it is meant that the components are disposed with respect to each other so that they are held in a compact configuration within the carrier tube for expulsion into the interior of the vessel, duct, lumen or tubular organ. Once expelled they are movable or positionable with respect to each other and with respect to the wall of the vessel, duct, lumen or tubular organ to assemble them in their "deployed state." In the deployed state the portions are oriented with respect to each other so that they are resistant to accidental dislodgement within the opening in the wall of the vessel, duct, lumen or tubular organ. In particular, the anchor member, lying against the interior wall of the vessel, duct, lumen or tubular organ contiguous with the opening prevents the deployed connector assembly from falling out of that opening.

In FIG. 4 there is shown an alternative embodiment of a connector assembly 222 constructed in accordance with this invention. The assembly 222 is similar in many respects to the connector assembly 22, but in other ways differs. In this connection, the connector assembly 222 includes components which are preassembled so that they are connected to each other prior to deployment. These preassembled components are held in a compact or "stowed" state within the carrier tube 82 so that they can be ejected from the carrier tube as a unit into the interior of the vessel, duct, lumen or tubular organ. Once ejected, the connector assembly 222 can then be retracted in a similar manner to that described heretofore to bring a portion of it into engagement with the wall of the vessel, duct, lumen or tubular organ contiguous with the opening 14 while another portion extends out to that opening for connection to the second connector member 64. The connector assembly 222 basically comprises a first connector member 224, an anchor member 62 and a second connector member 64. The anchor member 62 and the second connector member are identical to those components making up the connector assembly 22. Thus, in the interest of brevity, the details of the anchor component 62 and the second connector component 64 will not be reiterated and the various portions of these components will be given the same reference numerals as given previously.

The first connector member 224 is preferably formed of the same material as that of the anchor member 62. Moreover, the first connector member 224 includes various portions which are constructed similar to the connector member 60 of connector assembly 22. Thus, in the interest of brevity, the portions of the first connector assembly 224 which are similar to those portions of the first connector 60 will be given the same reference numerals. In particular, the first connector member 224 is a tubular member having a central passageway 72 extending through it. The distal end of the connector member 224 is in the form of an annular flange 84 while the proximal end is in the form of a chamfered surface detent 76. The outer surface of the connector between the flange 84 and the detent 76 is of circular profile and extends through the central opening 68 in the anchor member 62 so that the connector member 224 is slidable longitudinally within that opening. The connector assembly 222 is arranged to be disposed in a compact or "stowed" position within the carrier tube 82 of the deployment instrument. In particular, the connector 224 is centered within the opening 68 in the anchor 62, as shown in FIG. 4 to ensure that it has the smallest cross sectional profile for disposition within the carrier tube.

A pair of apertures 226 extend radially inward through the flange 84 to enable the filament 66 to be coupled to the connector member 224. In particular, the filament section 66B extends through the open proximal end of the central passage 72 of the connector member 224 and out through one of the apertures 226. The filament section 66B extends into the other aperture 226. From that point, the filament section 66B extends through the passageway 72 and out the proximal end thereof. The proximal end portions of filament sections 66A and 66B extend through the guide-pusher and through the deployment instrument, as will be described later.

Deployment of the connector assembly 222 is accomplished in a similar manner to that of connector assembly 22. In this regard, the guide-pusher assembly is used to push the assembled connector 224 and anchor 62 out of the carrier tube so that the preassembled connector member 24 and the anchor member 62 are located within the interior of the vessel, duct, lumen or tubular organ. Retraction of the filament sections 66A and 66B brings the proximal end of the connector member 224 back through the opening 14 in the wall of the vessel, duct, lumen or tubular organ. Moreover, retraction of the filament sections causes the top or proximal surface of the anchor member 62 to move into engagement with the inner surface of the vessel, duct, lumen or tubular organ contiguous with the opening 14, thereby causing the anchor member to "hang-up" on that surface. Further, retraction of the filament sections moves the connector member 224 with respect to the anchor member, i.e., it causes the connector member to slide through the hole 68 in the anchor member, so that more of the connector member 224 extends out of the opening in the wall of the vessel, duct, lumen or tubular organ until its flange 84 engages the bottom or distal surface of the anchor member contiguous with the hole 68. At this time, the connector device 224 is fully deployed and ready for connection to the connector member 64 and the bypass graft 10 connected to that connector. That connection is accomplished in the same manner as with the connector assembly 22 described earlier.

In FIG. 5, there is shown another alternative embodiment 32 of a connector assembly constructed in accordance with this invention. The connector assembly 322 is somewhat similar to the connector assembly 222 in that it is preassembled, i.e., its first connector and anchor components are assembled or connected to each other, but are movable relative to each other during the deployment procedure. In the interest of brevity, the common components of the connector assembly 322 and connector assembly 222 and connector assembly 22 will be given the same reference numerals and the details of their construction and operation will not be reiterated.

Thus, as can be seen in FIG. 5, the connector assembly 322 basically comprises a first connector member 324 and an anchor member 326. The first connector member 324 and the anchor member 326 are an integral unit, with the anchor unit 326 being similar in construction to the anchor member 62. Thus, the anchor member includes a central hole 68. The first connector member 324 is a collapsible, e.g., a corrugated, tube having a central passageway 72 extending therethrough. The distal end of the corrugated tube 324 is in the form of a flange 328 which is received within a correspondingly shaped annular recess 330 extending about the hole 68 in the anchor member 326. The tube 324 is arranged to be held in its compact or "stowed" state as shown in FIG. 5 when it is within the carrier tube of the deployment instrument, and to be extended to its deployed state, as shown in FIG. 6, during its deployment.

The proximal end of the collapsible corrugated tube 324 is in the form of an annular collar 332 forming a detent having a chamfered surface 76. The collar 332 is fixedly secured to the proximal end of the corrugated tube 324.

The anchor member 326 is preferably formed of a resorbable material, like that of the anchor members described heretofore. The corrugated tube may also be formed of the same resorbable material. Alternatively, it may be formed of any conventional biocompatible material, such as Dacron mesh, providing that it is impervious to the flow of liquid through it so that fluid flowing through the central passageway 72 will not leak out the wall of the corrugated tube 324 much like a synthetic vascular graft.

A radially oriented aperture 334 is provided in the annular collar 332 through which the filament 66 extends so that one filament section 66B extends from one side of the aperture while the other filament section 66A extends from the other.

The connector assembly 322 is disposed within the carrier tube 82 in its compact state like that shown in FIG. 5, so that its anchor member is oriented parallel to the central longitudinal axis of the carrier tube and immediately distally of the distal end 90 of the guide-pusher member 86. The filament sections 66A and 66B extend back through the interior of the guide-pusher and through the deployment instrument. The connector assembly 322 is ejected from the carrier tube in the same manner as described with reference to the connector assemblies 22 and 222. Once ejected into the interior of the vessel, duct, lumen or tubular organ, the two filament sections 66A and 66B are retracted. As will be described later, to draw the collar 332 of the connector assembly 332 back through the opening 14 in the wall of the vessel, duct, lumen or tubular organ. Continued retraction of the filament sections cause the top or proximal surface of the anchor member 326 to engage the interior surface of the vessel, duct, lumen or tubular organ contiguous with the opening 14 to cause it to hang-up in the same manner as described earlier. Once the anchor hangs-up, continued retraction of the filament section cause the corrugated tube 324 to stretch or straighten out, thereby increasing the length of the tube from the state shown in FIG. 5 to the state shown in FIG. 6. Once the connector assembly 322 is in the fully deployed state shown in FIG. 6, the second connector member 64 and the bypass graft 10 connected to it can be secured to the assembly 322 in the same manner as described heretofore.

Figure 12:
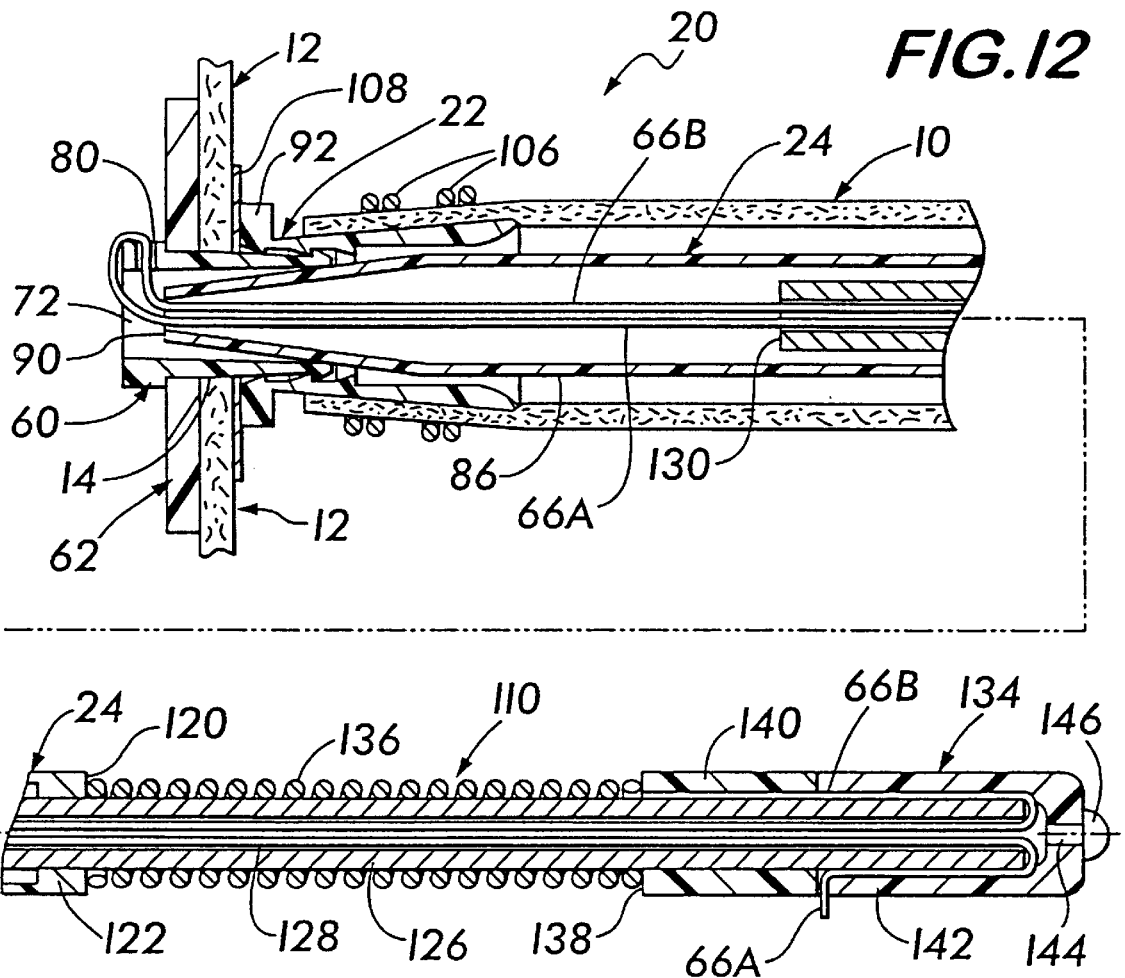
FIG. 12 is a longitudinal sectional view of the deployment instrument of FIG. 1 showing the formation of the anastomosis connection between the two vessels, ducts, lumens or tubular organs.

Referring now to FIGS. 1 and 12, the details of the deployment instrument 24 will now be described. Thus, as can be seen the deployment instrument 24 basically comprises the heretofore identified carrier tube 82 and the heretofore described pusher-guide assembly. That assembly includes the pusher-guide member 86 and an actuation assembly 110.

The carrier tube 84 includes an annular ring or stop 112 secured about is outer periphery immediately adjacent the proximal end 114. The stop 112 is provided to ensure that the carrier tube of the deployment instrument is not extended too far into the introducer sheath 28. Thus, the stop is arranged to engage the rear wall 38 of the hemostasis valve when it is in proper position.

The proximal end 114 of the guide tube is in the form of an inwardly extending, annular wall 116 having a central passageway 118 therein. The passageway 118 is adapted to closely receive the outer surface of the cylindrical portion of the pusher-guide member 86 to form a generally fluid-tight seal therebetween. The proximal end 120 of the pusher-guide member 86 is in the form of an inwardly extending annular wall 122 having a central passageway 124 therein. The central passageway 124 is arranged to closely receive a portion of the actuation assembly 110 (to be described hereinafter) to form a generally fluid tight seal therebetween.

The actuation assembly 110 basically comprises an elongated cylindrical mandrel rod 126 having a central passageway 128 extending along its length between its open distal end 130 and its open proximal end 132. The passageway 128 communicates with the interior of the pusher-guide member 86. An actuation cap 134 is mounted on the proximal end of the mandrel rod, with a helical compression spring 136 extends about the outer periphery of the hollow mandrel rod 126 interposed between the proximal end 120 of the pusher-guide tube 86 and a stop surface 138 forming the distal end of the actuation cap 134. The cap 134 basically comprises a pair of hollow tubular sections 140 and 142. The section 142 is disposed proximally of section 140 and is cup-shaped. The section 140 is fixedly secured to the mandrel rod 126 with the distal end of the filament section 66B tightly interposed therebetween. In particular, filament sections 66A and 66B extend from the connector assembly 22 through the pusher-guide member 86 into the hollow interior of the mandrel rod 126 and out the proximal end opening 132 of the passageway 128 extending through the mandrel rod 126. The distal end portion of filament 66B extends under the cup-shaped cap section 142 and is trapped between the outer surface of the mandrel rod 126 and the inner surface of the cap shaped 140. The distal end of the filament section 66A also extends out the proximal end 132 of the passageway 128 and is trapped between the outer surface of the mandrel tube 128 and the inner surface of the cup-shaped portion 142 of the cap 134. The cup-shaped portion 142 of the cap is removable for reasons to be described later.

The cap 134 also includes a central aperture in its end wall in communication with the interior passageway 128 of the mandrel tube 126. A plug, formed of a resilient material, such as rubber, is releasably located within the aperture 144 to seal it. The aperture 144, with the plug removed serves as a means to enable the deployment instrument 24 to determine the location of the wall of the vessel, duct, lumen or tubular organ as will be described later.

Figure 8:
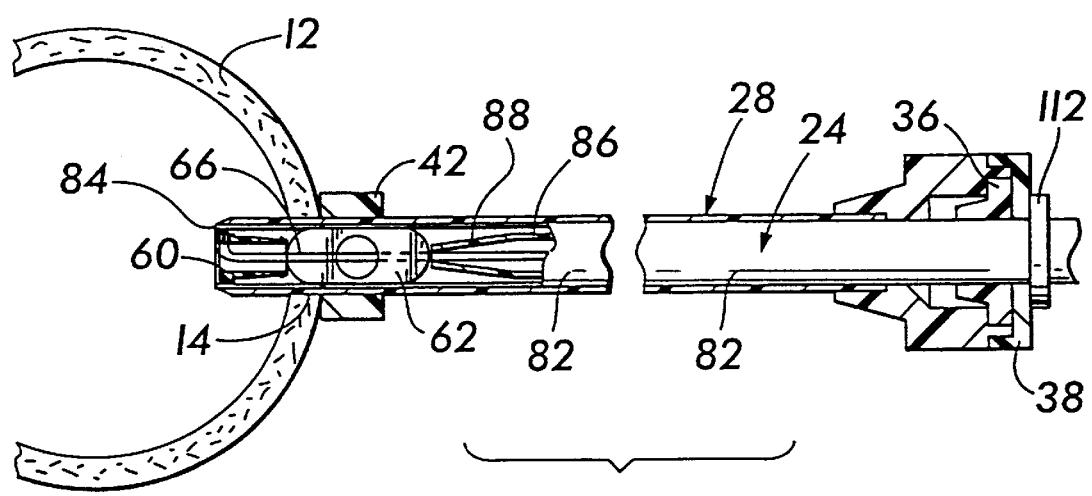
FIG. 8 is a longitudinal sectional view, similar to FIG. 7, but showing the deployment instrument extending through the introducer sheath to deploy the connector assembly of FIG. 1 into the interior of the vessel, duct, lumen or tubular organ.

Operation of the deployment instrument 24 is as follows:

The instrument is inserted into the introducer sheath after the sheath has been positioned with the piercer-dilator to form the opening 14 in the wall of the vessel, duct, lumen or tubular organ and the piercer-dilator has been removed. To that end, the deployment instrument is extended through the introducer sheath which is positioned as shown in FIG. 7 until the stop ring 112 on the deployment instrument 24 abuts the proximal end 38 of the hemostasis valve of the introducer sheath 28, as shown in FIG. 8. The cap 134 of the actuation assembly 110 is then pushed in the distal direction, thereby imparting movement in the distal direction to the pusher-guide tube 86 via the interposed spring 136. This action causes the free distal end 90 of the guide-pusher member to engage the proximal end of the anchor member 64 of the connector assembly 22 within the carrier tube 82. Continued pushing on the cap in the distal direction causes the pusher-guide member to eject the first connector member 60 and the anchor member 62 as described heretofore. Once the connector assembly's components are free of the guide tube and are located within the interior of the vessel, duct, lumen or tubular organ, the spring in attempting to assume its uncompressed natural state, applies tension to the filament sections 66A and 66B. In particular, the release of pressure on the cap 136 allows the spring to move from its compressed state shown in FIG. 1 to a longitudinally expanded or uncompressed state shown in FIG. 12. Since the filament ends are trapped by the cap 134, this action pulls the filament sections in the proximal direction, thereby drawing the components 60 and 62 of the first connector assembly 22 into the deployed state shown in FIGS. 9 and 10. Once the components are in this state, the introducer sheath is withdrawn, i.e., pulled off the instrument, leaving the deployment instrument 24 in the position shown in FIG. 12.

The second connector member 64 with the bypass graft 10 secured thereto is then threaded and slid down the instrument 24 over the actuation assembly and the pusher-guide tube to the position shown in FIG. 12. If a hemostatic washer 108 is used, as is preferable, that washer is threaded on the deployment instrument in advance of the second connector member 64.

When the second connector member 64 and the associated bypass graft 10 are slid in a distal direction until the flange 92 either directly engages the anchor surface of the wall of the vessel, duct, lumen or tubular organ or indirectly engages it via an interposed hemostatic washer 108. One of the chamfered detents of the second connector member 64 will be engaged by chamfered detent 76 of the first connector member 60 to secure the first and second connector members together.

Once the connector members 60 and 62 are connected together, the deployment instrument 24 can be removed to leave the anastomotic connection in position. To that end, the cup-shaped portion 142 of the actuating cap 134 is removed, thereby freeing the proximal end of filament section 66A. The remaining portion 142 of the cap 146 is then pulled or withdrawn in the proximal direction to withdraw the deployment instrument from within the interior of the bypass graft 10. Since the proximal end of filament section 66A is no longer trapped but the proximal end of the filament section 66B is trapped by the cap section 140 retraction of the instrument 24 causes the filament section 66A to move down the passageway 128 of the mandrel tube. Eventually, the free end of section 66A will pass through the aperture 80 in the first connector member 60 and from there will be pulled through the passageway 72 of that member and through the bypass graft interior until it exits the proximal end of the graft. At this point, the deployment instrument 24 will be fully removed from the anastomotic connection, leaving that connection in the state shown in FIG. 14.

The proximal end (not shown) of the bypass graft 10 can be secured to the occluded coronary artery (not shown) distally of the occlusion by any suitable technique. For example, the distal end of the bypass graft can be surgically connected to the coronary artery, or it can be connected utilizing means similar to that described herein introduced via an access port or slit (not shown) made in the wall of the bypass graft or by means such as taught in our co-pending U.S. patent application identified above.

As mentioned earlier, the actuation cap 134 of the deployment instrument 24 includes an aperture 144 which is sealed with a plug 146. The aperture 144 enables one to determine if the deployment instrument is properly positioned with respect to the wall of the vessel, duct, lumen or tubular organ. This action is accomplished by removing the plug 146 from the aperture so if the instrument is disposed at the desired position it will be in communication with the interior of the vessel, duct, lumen or tubular organ. Accordingly, blood will be enabled to flow from the interior of the vessel, duct, lumen or tubular organ and through the hollow interior of the pusher-guide member, and the communicating passageway in the mandrel tube where it exits the proximal end of that passageway and through communicating port 144.

Thus, when a drop of blood or other fluid appears at the port, the user of the instrument 24 knows that the device is in the desired position. The plug 146 can then be reinserted into the aperture 144 to seal it so that no further blood can gain egress through the instrument 24.

It should be pointed out at this juncture that the piercer-dilator instrument 26 may be constructed to utilize a similar flashback construction to provide an indication of proper placement, by the egress of a drop of blood from the proximal end of the piercer-dilator. More likely, the formation of the opening in the wall of the vessel, duct, lumen or tubular organ will be preformed under direct vision. If a fluid flashback system is incorporated into piercer-dilator, or the introducer sheath, it will allow placement of the introducer sheath at a specific location within the vessel, duct, lumen or tubular organ without the need for direct observation.

It must be pointed out at this juncture that it is contemplated that the connector assemblies of this invention could be actively assembled or deployed by manual pulling of the filament sections and pushing on the pusher member instead of using a spring loaded system like described heretofore.

The bypass graft 10 is prepared by inserting the proximal end of the second connector member 64 into the open distal end of the graft section 10. The connector is held in place by use of one or more stainless steel spring clips 106. The spring clips and the second connector 64 are preferably available in different sizes to cater to different graft sizes. In particular, the spring clips 106 are sized to a predetermined inside diameter to limit the constriction of the graft which would otherwise cause necrosis of the interposed tissue due to excessive pressure. Other means can be utilized to secure the graft 10 to the second connector member 64. Such means may be a biocompatible adhesive, pre-knotted suture loops, sutures, c-clips, etc.

The inside profile of the passageways of the connector assemblies of this invention are preferably designed to minimize turbulence and control the pressure of fluid flowing therethrough, such as disclosed in our heretofore identified co-pending patent application. It should also be pointed out that the various connector components of the connector assemblies of this invention can be coated with, or impregnated with chemicals, drugs, or other biologically active components to affect the nearby tissue or cells. Such active components could include, but are not limited to, anti-platelet drugs, antimicrobial agents, antibiotics, anti-thrombogenic materials, antioxidants, growth factors, growth hormones, genetic material, or seeded cells.

It should be noted that the embodiments of the connector assemblies and/or the deployment instrument and/or the piercer-dilator instrument, and/or the introducer sheath as shown and described heretofore are merely exemplary. Thus, other constructions are contemplated. For example, the anchor member may be shaped other than a linear strip, e.g., it may be slightly arcuate or trough-shaped like that disclosed in our aforementioned copending application. The positioning member for the connector assemblies may comprise other types of components making use of at least one filament or may comprise other devices, such as a flexible wire having a balloon on its distal end. The connector assemblies and/or the components thereof need not be formed to be totally resorbable. Thus, none or only portions of such assemblies may be resorbable.

Figure 15:
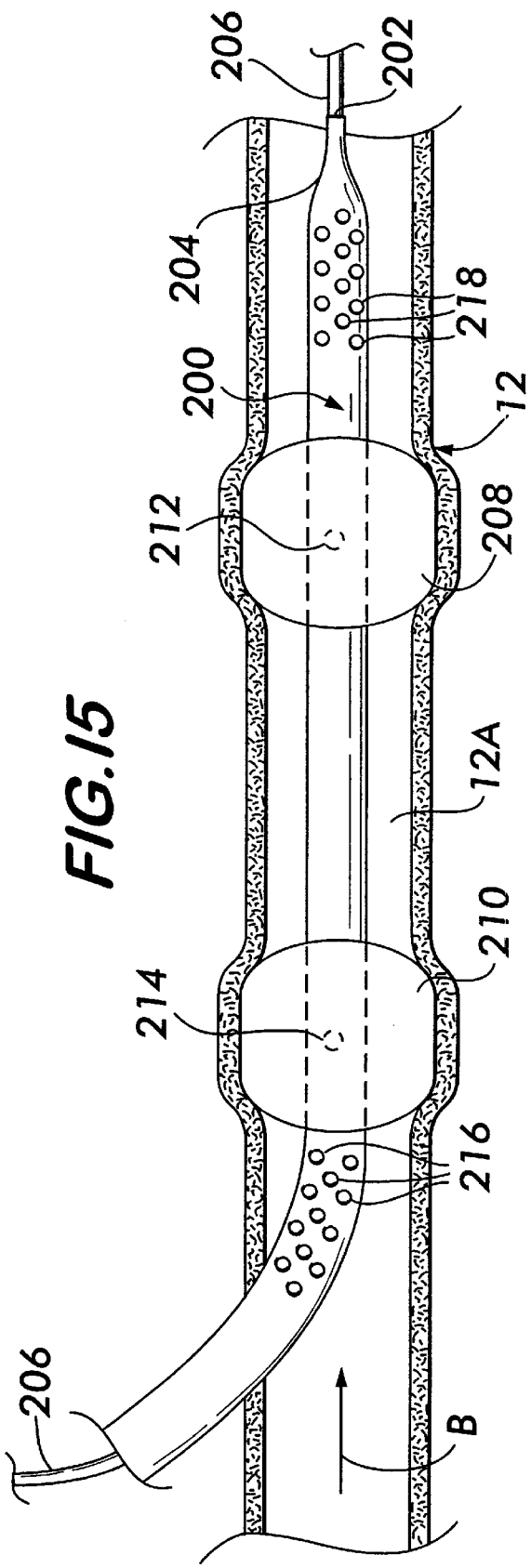
FIG. 15 is a longitudinal sectional view of an isolation instrument located within a vessel, duct, lumen or hollow body of a living being to temporarily preclude blood or other fluid from flowing therethrough to facilitate the formation of an anastomosis connection or to accomplish some other procedure on the wall of the vessel, duct, lumen or hollow organ.

During a coronary or other vascular bypass procedure involving the use of an anastomosis connector, it is desirable to isolate an area within the vessel contiguous with the site at which the anastomosis is to be made from the passage of blood therethrough. Such action facilitates the procedure by obviating the necessity to constantly swab or otherwise remove blood from the site and also provides a better visual field for the surgeon. In FIG. 15 there is shown one embodiment of an instrument which may be used during the anastomosis procedure to achieve that end, i.e., preclude blood, from flowing through a portion of the blood vessel contiguous with the anastomosis site. It should be pointed out at this juncture that the instrument shown in FIG. 15 and the other instruments to be described later are not limited to use in an anastomosis procedure on a blood vessel. Thus, the instrument 15 and the other instruments to be described hereinafter (all collectively referred to as "isolation instruments") can be used to preclude the flow of blood or any other body fluid through a vessel, duct, lumen or hollow organ in the body of a living being while some type of surgical procedure is accomplished on the wall of that vessel, duct, lumen or hollow organ. For example, as will be described later the isolation instrument of FIG. 15 (and any other instrument constructed in accordance with the teaching of this invention) can be utilized to isolate a portion of the interior of a vessel, duct, lumen or hollow organ while an opening in the wall thereof is sutured to seal the opening.

In FIG. 15 one embodiment of an isolation instrument 200 constructed in accordance with this invention is shown in its deployed or operative state within a vessel, duct, lumen or hollow organ 12 to isolate a portion 12A thereof. This isolated are can serve as an anastomosis site or the site of any other surgical procedure desired thereat. In the exemplary description to follow the procedure entails forming an anastomosis connection at portion 12A utilizing the anastomosis connector 22 described heretofore. In the interest of brevity the details of the construction and the manner of deployment of that connector will not be reiterated.

As can be seen the isolation instrument 200 basically comprises an over-the-wire dilator in the form of an elongated flexible body having a central passageway 202 extending longitudinally therethrough. The distal end of the instrument is tapered at 204. A conventional guide wire 206 is arranged to be extended through the passageway 202 to effect the placement of the instrument 200 at the desired position within the vessel, duct, lumen or hollow organ 12. A pair of conventionally constructed inflatable balloons 208 and 210 are mounted on the elongated body, with the balloon 208 being located closely adjacent the tapered distal end portion 204 and with the balloon 210 being located a short distance proximally of the balloon 208. As will be appreciated from the discussion to follow the spacing between the balloons 208 and 210 defines the longitudinal extent of the fluid exclusion zone, i.e., the zone 12A from which blood or other fluid will be temporarily precluded from flowing. One or more inflation/deflation passageways (not shown) extend (s) down through the body of the instrument 200 and terminate(s) in a pair of balloon inflation ports 212 and 214. The port 212 is located within the balloon 208 and the port 214 is located within the balloon 210.

Figure 33:
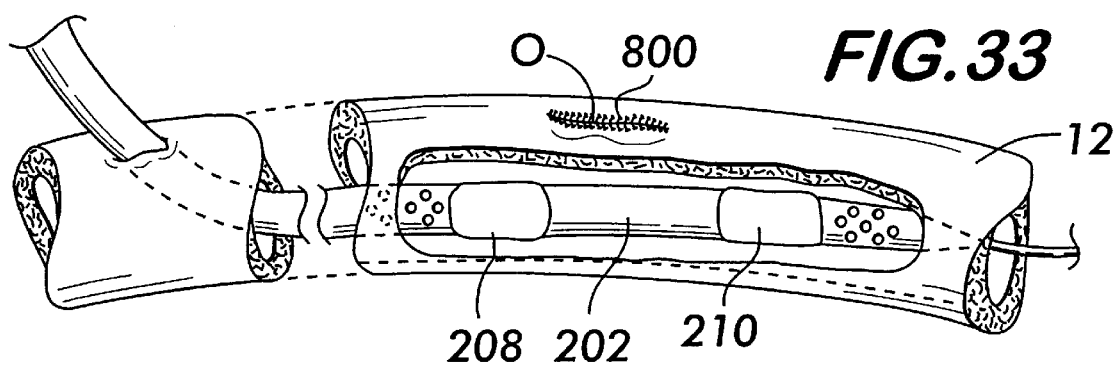
FIG. 33 is a view similar to FIGS. 31–32 but showing the isolation instrument in a state ready to be removed after the opening has been sutured.

The balloons are arranged to be inflated in a conventional manner from a compact state, like that shown in FIG. 33, to the expanded state like that shown in FIG. 15 via the inflation/deflation passageway(s) and associated ports 212 and 214. When the balloons 208 and 210 are in their inflated state, they engage the interior of the vessel, duct, lumen or hollow organ about their entire periphery. Thus, blood or other body fluid B which is flowing through the vessel, duct, lumen or hollow organ in the direction of the arrow shown in FIG. 15 will be blocked by the inflated balloon 210 from flowing distally therebeyond. In a similar manner any fluid distally of the inflated balloon 208 will be precluded by that balloon from flowing proximally of that balloon. Accordingly, blood or other body fluid cannot gain ingress into the space 12A between the balloons 208 and 210 once they are inflated.

If it is desired to enable blood or other body fluid to flow from upstream of the balloon 210 to points downstream of the balloon 208, such as is case when performing an coronary anastomosis in order to continue to perfuse downstream tissue, the isolation instrument 200 may include a shunt path for such fluid flow, while still precluding blood or other body fluid from entering into the fluid-exclusion zone 12A. To that end, the instrument 200 preferably includes a bridging passageway (not shown) extending longitudinally through the body of the instrument from a point just proximally of the balloon 210 where the passageway communicates with one or more inlet apertures 216 to a point just distally of the balloon 208 where the passageway communicates with one or more outlet apertures 218. Each of the apertures 216 is in fluid communication with the interior of the vessel, duct, lumen or hollow organ upstream of the balloon 210. Likewise, each of the apertures 218 is in fluid communication with the interior of the vessel, duct, lumen or hollow organ downstream of the balloon 208. Accordingly, blood or other body fluid B flowing down the vessel, duct, lumen or hollow organ 12 will enter into the apertures 216 and the communicating bridging passageway and exit through the apertures 218 distally of the balloon 208 where it can continue to flow downstream.

Figure 16:
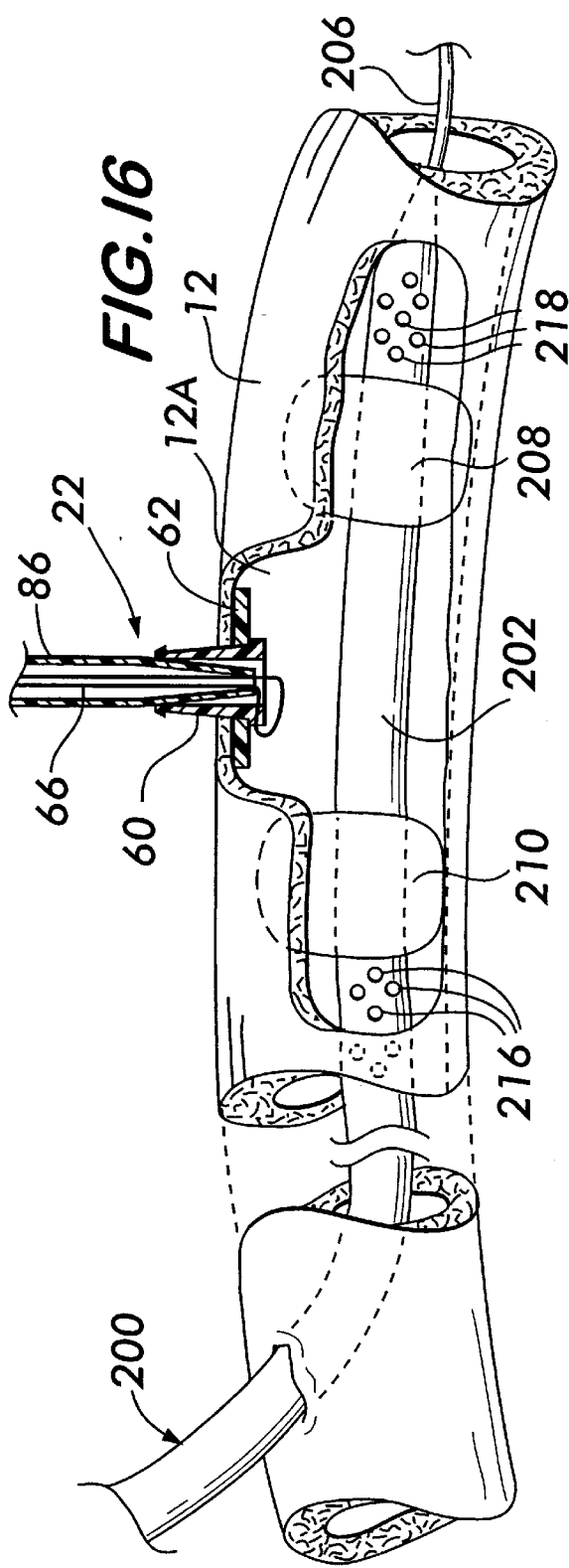
FIG. 16 is a view similar to FIG. 16 but showing the isolation instrument during the formation of an anastomosis connection utilizing the embodiment of an anastomosis connector shown in FIGS. 1–3.

The use of the isolation instrument 200 to effect an anastomosis connection within a vessel, duct, lumen or hollow organ 12 is shown in FIG. 16 and basically entails, introducing the instrument to the situs for the anastomosis connection via the guide wire 206. Once the instrument is in position it is inflated, as described with reference to FIG. 15 to create the fluid-exclusion zone 12A. Once the instrument 200 is in place and operated, i.e., its balloons inflated, the anastomosis connector 20 can be deployed in the same manner as described heretofore. Since fluid, e.g., blood, will be precluded from flowing into the space 12A by the deployed balloons, any blood within that space can be swabbed or otherwise removed, e.g., flushed with an irrigant, upon penetration of the piercing instrument 26 and/or the introducer sheath 28 through the wall of the vessel, duct, or lumen. Since no blood or other fluid will flow into this space while the balloons are inflated the deployment, orientation and connection of the anastomosis connector 22 can proceed uninhibited. In addition the lack of blood at the anastomosis site should provide the surgeon with a better view of the procedure as it is accomplished.

Once the anastomosis connection has been completed, the balloons 208 and 210 may be deflated, and the isolation instrument withdrawn from the interior of the vessel, duct, lumen or hollow organ.

If the anastomosis procedure requires fluid, e.g., blood perfusion, downstream of the anastomosis site such action can be accomplished by providing the desired fluid via the shunt path comprising the inlet apertures 216, the bridging passageway, and the outlet apertures 218 as described above. Such perfusion can occur all the while that the balloons are inflated.

In FIG. 17 there is shown the formation of an anastomosis connection employing an anastomosis connector 400 like that of the '584 application and using the isolation instrument 200 to create a fluid preclusion zone within the vessel, duct, lumen, or hollow organ forming the anastomosis site.

All of the details of the construction and operation of the connector 400 will not be described herein in the interest of brevity. Suffice it to state that the connector 400 basically comprises a tubular proximal portion 402 and a culvert shaped member 404 located on the distal end of the tubular portion 402. The tubular portion 402 includes a passageway 406 extending through it and which terminates at the culvert member 404. The culvert member 404 has front end portion 408 and a rear portion 410. The front end portion 408 is arranged to be inserted through an opening or slit S formed in the wall of the vessel, duct, lumen or hollow organ 12 and slid forward until the leading edge of the slit S abuts the tubular portion 402 where it merges with the culvert member 404. The length of the culvert member 404 from the merger point to the edge of rear portion 410 is selected to be approximately equal to the length of the slit S measured in the longitudinal direction. Thus, the distal edge of the culvert portion can be introduced through the slit S and slid forward until the distal edge of the slit S abuts the merger point, whereupon the anastomosis connector 400 can be rotated downward or inward to cause the rear edge of culvert portion 404 to pass through the slit S until the connector is oriented such that the longitudinal axis of the culvert member is parallel to the longitudinal axis of the vessel, duct, lumen or hollow organ 12. The anastomosis connector 400 can then be retracted or pulled proximally within the vessel, duct, lumen or hollow organ so that the tubular portion 402 abuts the trailing end of the slit S. In this position part of the front portion of the culvert member 404 will underlie a portion of the vessel, duct, lumen or hollow organ contiguous with the leading edge of the slit and the rear portion of the culvert member will underlie the vessel, duct, lumen or hollow organ contiguous with the trailing edge of that slit, thereby preventing the anastomosis connector 400 from being pulled out.

Figure 29:
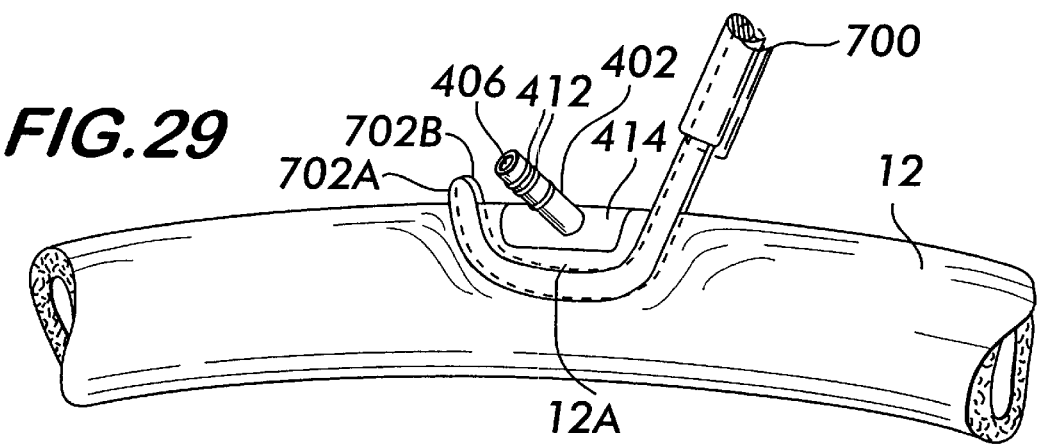
FIG. 29 is a view similar to FIGS. 26–28 but showing a still later step in that process.
Figure 30:
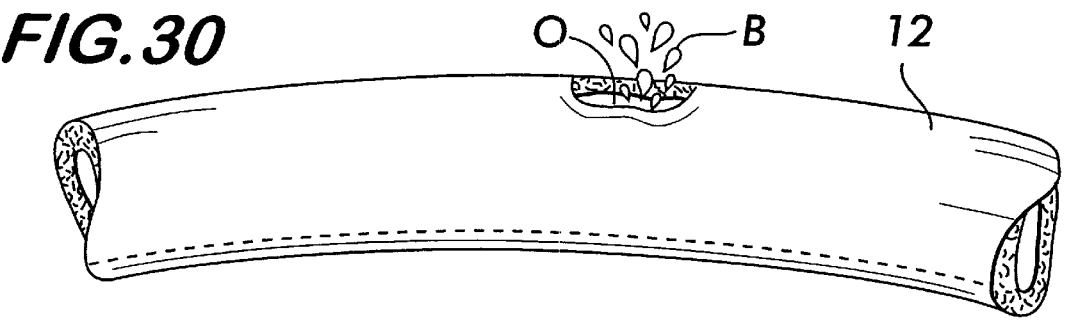
FIG. 30 is an isometric view of a vessel, duct, lumen or hollow organ having an opening, e.g., a tear, in the wall thereof which is desired to be closed.

In order to further lock the anastomosis connector 400 in place, a culvert-shaped locking plate 414 (FIG. 29) is provided. The inside diameter of the locking plate is similar to the outside diameter of the vessel, duct, lumen or hollow organ so that it can engage a substantial portion of the periphery thereof. The locking plate also includes an opening through which the tubular portion 402 of the connector 400 is threaded. The locking plate is arranged to engage detents (not shown) on the tubular member to lock it in place, whereupon the wall of the vessel, duct, lumen or hollow organ is sandwiched and locked between the locking plate and the interiorly located culvert-shaped member 404.

The proximal end of the tubular member 402 includes snap-connection means 412 in the form of annular detent rings to secure that end of the connector 400 to a mating connector (not shown) on the end of a bypass graft or some other vessel, duct, lumen or hollow organ.

In FIG. 18 there is shown an alternative isolation instrument 300 constructed in accordance with this invention. Unlike the instrument 200, the instrument 300 is arranged to engage portions of the vessel, duct, lumen or hollow organ from the exterior thereof to form the fluid-exclusion zone within the vessel, duct, lumen or hollow organ. Thus, the instrument 300 basically comprises a tubular body 202 like that of the instrument 200, but without the inflatable balloons. The tubular body includes the heretofore identified central passageway 206 for the guide wire, the inlet apertures 216, the bridging passageway (not shown) and the outlet apertures 218. The body 202 is arranged to be located within the vessel, duct, lumen or hollow organ in the same manner as described with reference to isolation instrument 200.

A pair of clamps 302 and 304 are provided on the outside of the vessel, duct, lumen or hollow organ to tightly squeeze the wall thereof between them and the body 202 of the instrument to produce the fluid-exclusion zone 12A in the vessel, duct, lumen or hollow organ. To that end the clamp 302 basically comprises a hollow tube 306 and a flexible filament 308. The filament 308 is extended down the interior of the tube 306, about the periphery of the exterior of the wall of the vessel, duct, lumen or hollow organ at the position defining the upstream end of the fluid-exclusion zone 12A, and back through the interior of the tube 306. By pulling on both ends of the filament the loop extending about the vessel, duct, lumen or hollow organ tightens to tightly sandwich the wall between it and the exterior surface of the body 202 of the instrument 400 which is located within that vessel, duct, lumen or hollow organ. In a similar manner the clamp 304 basically comprises a hollow tube 310 and a flexible filament 312. The filament 312 is extended down the interior of the tube 310 and about the periphery of the exterior of the wall of the vessel, duct, lumen or hollow organ at the position defining the downstream end of the fluid-exclusion zone 12A, and back through the interior of the tube 308. Operation of the clamp 304 is the same as that of clamp 302.

In FIG. 19 there is shown another alternative embodiment of an isolation instrument 500 constructed in accordance with this invention. The instrument 500, like the instrument 300, is arranged to engage the exterior of the vessel, duct, lumen or hollow organ. However, unlike the instrument 300, the instrument 500 is arranged to be located totally outside the vessel, duct, lumen or hollow organ. Thus, the instrument 500 doesn't make use of any over-the-wire dilator body 202 or other device located with the interior of the vessel, duct, lumen or hollow organ. The isolation instrument 500 does, however, includes means to stabilize it adjacent the vessel, duct, lumen or hollow organ during its operation. This later features makes the instrument 500 particularly suitable for effecting an anastomosis of a coronary artery, such as is accomplished during bypass surgery. An exemplary coronary artery is shown in FIG. 22 and designated by the reference number 12C and is shown located in the epicardium 12D of the heart 12E.

Returning now to FIGS. 19–21 it can be seen that the instrument 500 basically comprises a base or stabilizing member in the form of a yoke shaped, arcuate plate 502 and a pressure applicator or compressor member also in the form of a yoke shaped arcuate plate 504. The compressor member 504 is disposed over the stabilization member 502 and is movable with respect thereto. The stabilization member includes a pair of spaced apart arms 502A and 502B, each of which includes a respective hole 506 therein. A plurality of suction cups 508 are located on the undersurface of the base member 502 contiguous with the arms 502A and 502B. Each of the suction cups is coupled via a tube 510 to an externally located vacuum source (not shown). The upper end of the stabilization member 502 is connected to a handle 512.

The compressor member 504 is curved similarly to the stabilization member 502 and also includes a pair of spaced apart arms 504A and 504B. A rod-like pressure applicator or foot projects 514 downward from the undersurface of each of the arms 504A and 504B. Each of the feet 514 is arranged to be extended through a respective hole 506 in the arms 502A and 502B of the stabilization member 502.

A plurality of small nubs or protuberances 516 extend outward at equidistantly spaced locations from the upper surface of the compressor member 504. The protuberances are aligned in a row. A resilient band 518 extends about the upper portion of the stabilization member 502 and the compressor member 504. The band includes an aperture 520 to receive one of the protuberances 516 to lock the two members 502 and 504 with respect to each other. The upper end of the compressor member 504 terminates in a handle 522.

Operation of the instrument 500 will be described in connection with the formation of an anastomosis connection at a coronary artery, like 12C in FIG. 22. In particular, the isolation instrument 500 is arranged to be mounted with respect to the heart and stabilized in position so that it can create a fluid-exclusion zone within the coronary artery at the situs of the proposed anastomosis. In order to stabilize the instrument 500 the handle 512 at the top of the stabilization member 502 is arranged to be connected to some means, e.g., a conventional retractor ring, (not shown) fixedly secured to the body of the patient undergoing the anastomosis. Prior to connecting the instrument to such means, the instrument 500 is moved into position, like shown in FIG. 20, so that the plural suction cups 508 on the underside of the arms 502A and 504A engage the epicardium immediately adjacent the proposed anastomosis site and with the openings 506 in the arms 502A and 502B being disposed over the coronary artery section to be anastomosed. In particular, the instrument is positioned so that the opening 506 in the arm 502A is located at the upstream end of the anastomosis site, i.e., to be formed fluid-exclusion zone, while the opening 506 in the arm 502B is located at the downstream end of that zone. Suction is then applied to the suction cups 508 via the lines 510 to stabilize the instrument 500 with respect to the heart.

The handle 512 of the instrument 500 can then be secured to the retractor ring or any other suitable member fixed in position with respect to the patient. Once this has been accomplished the handle 520 of the compressor member 502 can then be pressed downward, with respect to the handle 512, thereby moving the compressor member's arms 504A and 504B closer to the stabilization member's arms 502A and 502B, respectively. This action causes the pressure applicator feet 514 to pass through the respective holes 506 in the stabilization member's arms to engage the underlying exterior surface of the coronary artery 12D. Continued downward movement of the pressure applicator member with respect to the base member causes the projecting rods or feet 514 to collapse the coronary artery 12C at their respective points of engagement as shown in FIG. 21. Thus, coronary artery will be collapsed, and hence occluded, at the two pressure application points, but with the space within the artery between those points, i.e., the fluid-exclusion zone, being uncollapsed. This action precludes blood from flow into the fluid-exclusion zone as long as the pressure is applied by the feet 514. In order to hold the two members 502 and 504 in this position the ring 518 is then slid up or down the instrument to receive one of the protuberances 516 within its hole 520.

The anastomosis connection can then be made in the wall of the uncollapsed coronary artery between the pressure application points using any type of anastomosis connector desired. It should be pointed out that the anastomosis procedure carried out at this site need not make use of an anastomosis connector, but may be made in a conventional manner, e.g., via sutures. Thus, it must be understood that the instrument 500, and any other isolation instrument of this invention, can be used to effectuate any type of anastomosis procedure, e.g., a conventional surgical anastomosis via sutures, at an anastomosis site which has been isolated from blood or other fluid flow.

Once the anastomosis has been completed the vacuum source can be released, thereby releasing the suction engagement of the isolation instrument's suction cups 508 on the epicardium. The handle 512 of the stabilization member 502 can then be dismounted from the retractor ring to enable the isolation instrument 500 to be removed, thereby releasing the pressure on the coronary artery wall at the two pressure points so that blood is enabled to flow therethrough.

Figures 23, 24, 25:
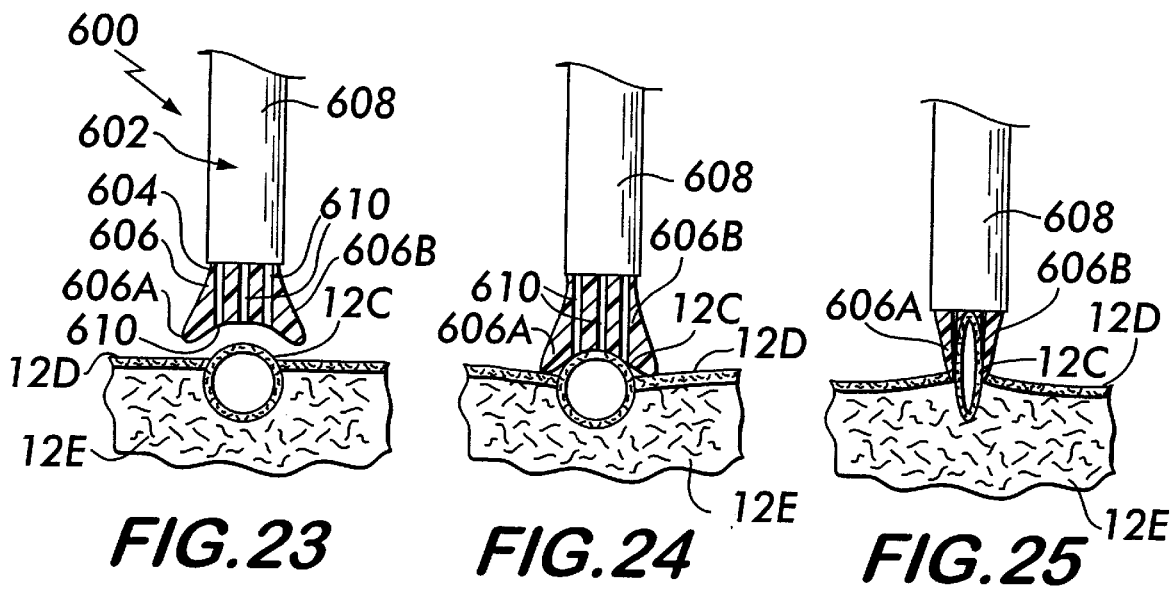
FIG. 23 is a partial sectional view showing yet another alternative embodiment of an isolation instrument constructed in accordance with this invention at an early step in the process of isolating a portion of a coronary artery (or other vessel, duct, lumen or hollow organ) to temporarily preclude the flow of blood or other fluid therethrough.
FIG. 24 is a view similar to FIG. 23, but showing the isolation instrument at a later step in that process.
FIG. 25 is a view similar to FIGS. 22 and 23, but showing the isolation instrument at a still later step in that process.

In FIG. 23 there is shown a portion of another alternative embodiment of an isolation instrument 600 constructed in accordance with this invention. The instrument 600 is similar in concept to the instrument 500, in that it is arranged to collapse the vessel, duct, lumen or hollow organ to create the fluid exclusion zone from outside the vessel, duct, lumen or hollow organ and without use of any device or means within that vessel, duct, lumen or hollow organ. The instrument 600 basically comprises two suction/deformation units 602, only one of which is shown. One unit is arranged to collapse the downstream end of exclusion-zone in the vessel, duct, lumen or hollow organ while the other unit is arranged to collapse the upstream end thereof. Each unit 602 basically comprises an elongated body member 604 having a suction head 606 located at the distal end thereof and a sleeve 608 slidably mounted on the body member 604. The sleeve 608 is located proximally of the head 606 in its normal, non-operative position or retracted position so that the head extends out of the open end of the sleeve. The suction head 606 is formed of a resilient material and has a pair of opposed lateral fingers 606A and 606B at the distal end thereof. Plural longitudinally extending passageways 610 extend through the body portion and terminate at the free end surface of the head 606 between the fingers 606A and 606B. The passageways 610 are in fluid communication with an externally-located vacuum source (not shown).

The units 602 may be coupled together for joint movement and positioning with respect to the vessel, duct, lumen or hollow organ on which the instrument will be used, or may be movable with respect to each other. In any case, each unit is arranged to be brought into engagement with the exterior wall of the vessel, duct, lumen or hollow organ. For example, when operating on a coronary artery 12C, as shown in FIG. 24 one unit 602 is brought over the coronary artery at the upstream end of the desire exclusion zone (e.g., anastomosis site). The unit is then moved downward so that its suction head engages the wall of the coronary artery and with its fingers 606A and 606B straddling that artery, i.e., with one finger 606A being on one side of the artery and the other finger 606B being on the other side. Suction is then applied to artery wall via the passageways in the suction head 606 of the unit. At the same time that suction is applied to the artery wall, the sleeve 608 of that unit is slid from its retracted position shown in FIGS. 23 and 24 in the distal direction to the extended or operative position shown in FIG. 25. The combination of the applied suction and the movement of the sleeve to the operative position causes the fingers 606A and 606B to collapse towards each other as shown in FIG. 25, thereby collapsing the artery wall between them. Operation of the other unit to collapse the artery wall at the downstream end of the exclusion zone is identical, and may be carried out simultaneously with the upstream end or at a different time, e.g., before or later.

Once both units have collapsed the artery to form the fluid-exclusion zone any surgical procedure, e.g., the formation of an anastomosis, can be carried out expeditiously. When that procedure is completed, the sleeves on the two units 602 can be retracted and the suction released, thereby allowing the artery to again carry blood therethrough.

Figure 26:
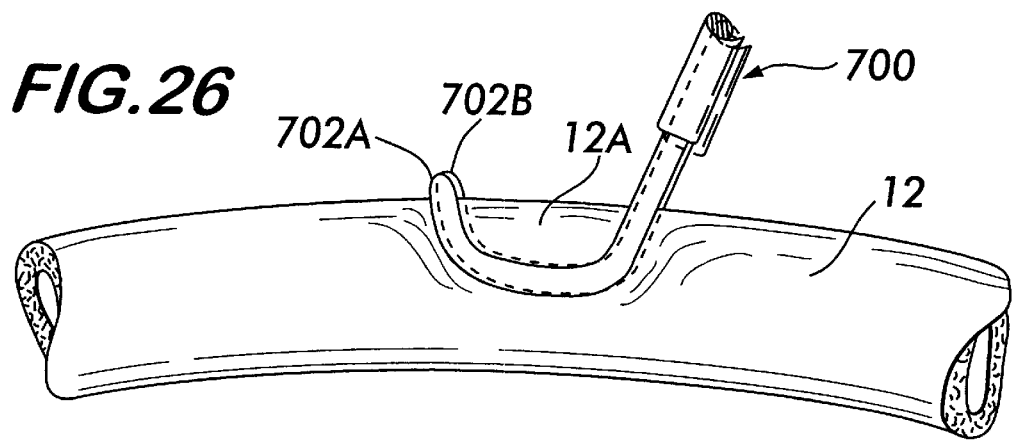
FIG. 26 is an isometric view of an early step in a process for forming an anastomosis connection utilizing an externally applied clamping device, e.g., a hemostat, forceps, etc., to temporarily preclude the flow of blood or other fluid through the vessel, duct, lumen or hollow organ while the anastomosis connection is being made.
Figure 27:
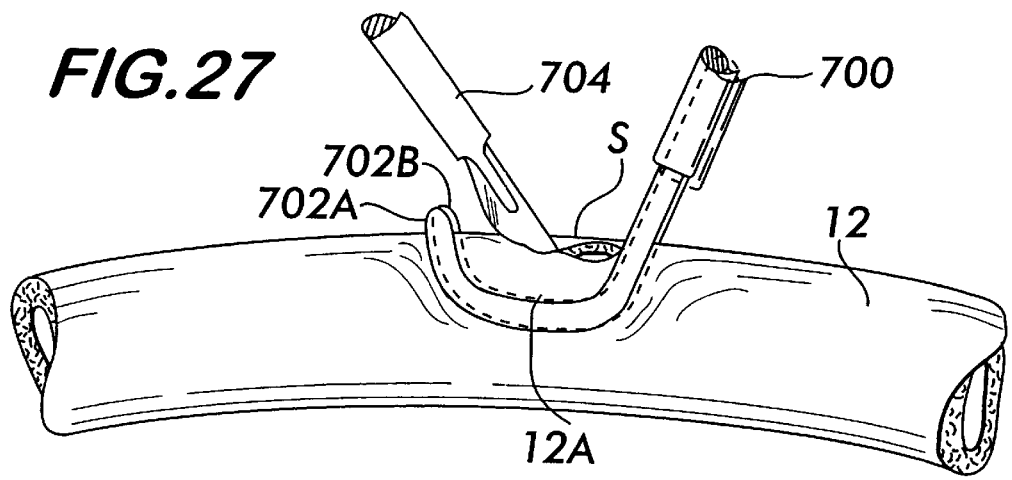
FIG. 27 is a is a view similar to FIG. 26, but showing a later step in that process.
Figure 28:
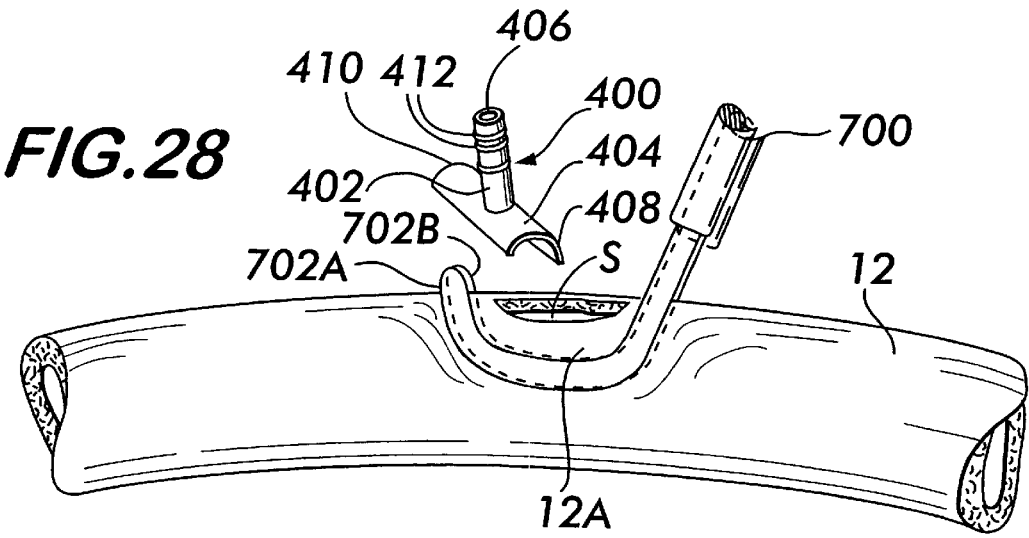
FIG. 28 is a view similar to FIGS. 26–27, but showing a still later step in that process, i.e., the placement of an anastomosis connector like that of FIG. 17 in a slit in the wall of the vessel, duct, lumen or hollow organ.

In FIGS. 26–30 there is shown a method of forming an anastomosis connection in a vessel, duct, lumen or hollow organ with an anastomosis connector 400 like that shown in FIG. 17, but utilizing a conventional instrument, e.g., a clamp 700, to form a fluid-exclusion zone during the anastomosis. To that end, as shown in FIG. 26 the clamp 700 is used to grasp and collapse only a portion of the periphery of the vessel, duct, lumen or hollow organ 12 between its generally U-shaped jaws 702A and 702B. Since the jaws are U-shaped the portion of the vessel, duct, lumen or hollow organ within the bounds of those jaws defines a fluid-exclusion zone 12A. Moreover, since the jaws only grasp a portion of the periphery of that vessel, duct, lumen or hollow organ, the portion outside the U-shaped jaws remains uncollapsed so that blood or other fluid can flow therethrough, while being precluded from flowing into the fluid-exclusion zone 12A. A conventional scalpel 704 may then be used to produce a incision or slit S in the wall of the vessel, duct, lumen or hollow organ within the exclusion-zone, as shown in FIG. 27.

The anastomosis connector 400, or any other type of anastomosis connector, can then be inserted within the slit S and secured in place. With respect to the connector 400, that connector is secured in place in the slit in the same manner as described earlier with reference to FIG. 17, while the jaws 702A and 702B of the clamp instrument 700 maintain pressure on the wall of the vessel, duct, lumen or hollow organ to maintain the exclusion-zone. Once the anastomosis connector 400 is in place and secured, like shown in FIG. 29, the retractor clamp 700 may be removed, i.e., its jaws opened, thereby enabling blood or other fluid to flow into the fluid-exclusion zone.

Figure 31:
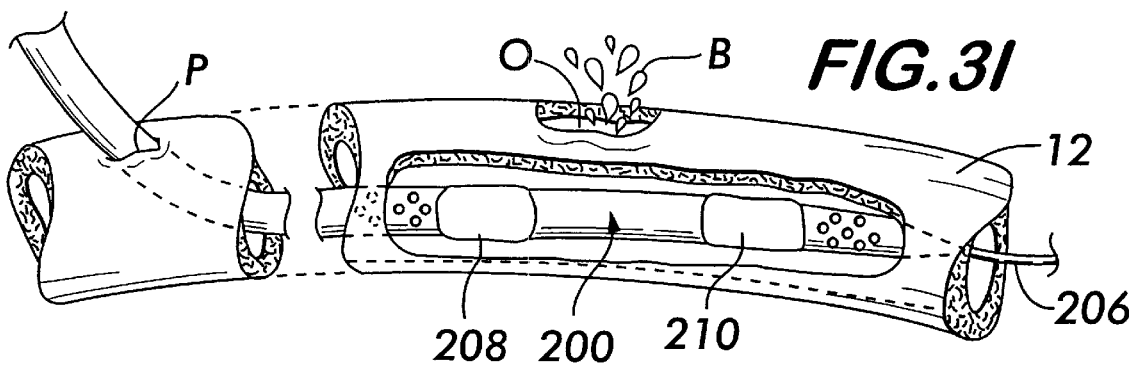
FIG. 31 is a longitudinal sectional view of the vessel, duct, lumen or hollow organ of FIG. 30 but showing the isolation instrument of FIGS. 15–17 located therein at an early step in the process of closing that opening by temporarily precluding the flow of blood or other fluid through a zone contiguous with the opening.
Figure 32:
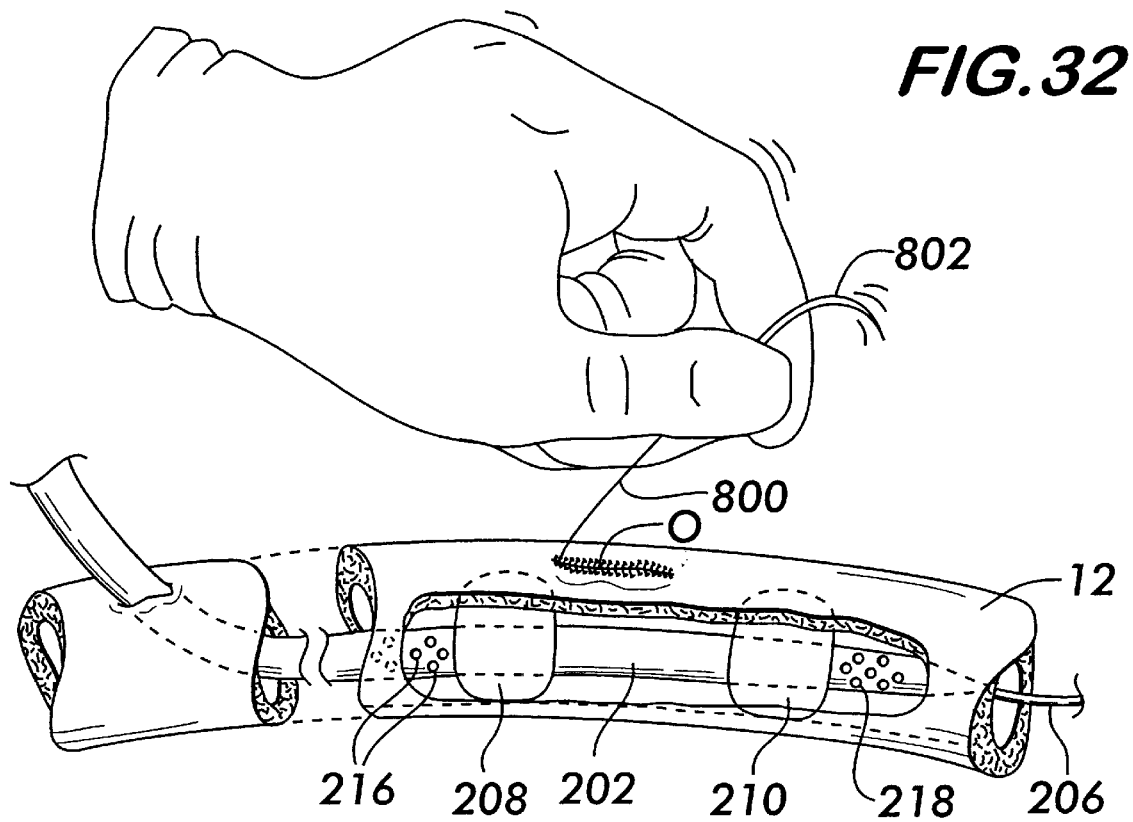
FIG. 32 is a view similar to FIG. 31 but showing the isolation instrument in operation temporarily precluding blood or other fluid from flowing through the zone while the opening is manually closed by suturing.

It should be pointed out at this juncture that the use of the exclusion instruments of this invention as described heretofore have focused on creating a fluid-exclusion zone to enable some anastomosis procedure to be accomplished at that zone. As mentioned earlier the use of the exclusion instruments of this invention is not so limited. Thus, those instruments can be used to create a fluid exclusion zone for accomplishing any type of surgical procedure on the wall of a vessel, duct, lumen or hollow organ. One such procedure is shown in FIGS. 30–34, wherein an opening in an artery wall is shown in the process of being sealed by conventional sutures. Thus, in FIG. 30 there is shown a vessel, duct, lumen or hollow organ, e.g., an artery 12, which includes an opening O, e.g., a rupture or tear, through which fluid, e.g., blood B, is leaking and which opening is desired to be sealed. As shown in FIG. 31, an isolation instrument, e.g., instrument 200, is extended over a conventional guide-wire 206 into the artery via a puncture or incision P adjacent to the opening O. If desired, the entry point P for the instrument 200 may be remote from the opening O and the instrument threaded through the vascular system from that entry point. Irrespective of the location of the entry point for the instrument, the balloons 208 and 210 are collapsed or uninflated when the instrument is introduced to facilitate its placement. In particular, the instrument 200 with its collapsed balloons is extended down the guide-wire through the interior of the artery until its balloon 210 is located distally of the opening O and its balloon 208 is located proximally of that opening. The balloons can then be inflated as shown in FIG. 32 to create the fluid-exclusion zone 12A therebetween. As described earlier, blood is enabled to flow downstream of the instrument by flowing into the inlet apertures 216, through the bridging passageway(s) and out through the outlet apertures 218 to downstream tissue, while the balloons preclude any blood from flowing into the fluid-exclusion zone. Thus, the surgeon can then close the opening using any conventional technique. In the exemplary embodiment of FIG. 32 the opening O is shown being closed by a conventional suture 800 connected to a conventional curved needle 802.

Figure 34:
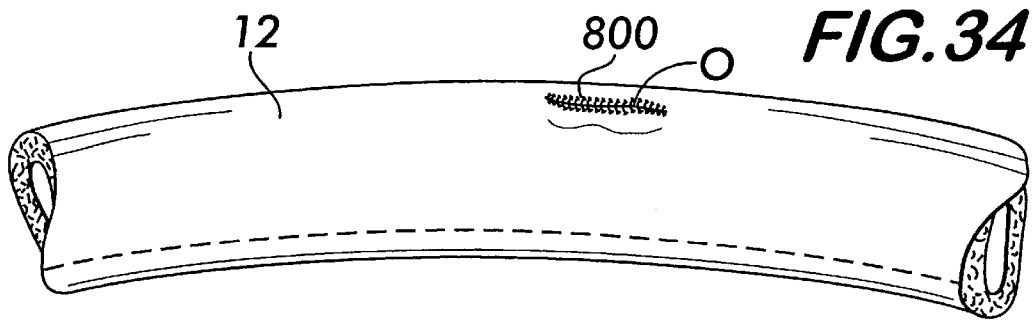
FIG. 34 is a view similar to FIG. 33, but showing the opening in the vessel, duct, lumen or hollow organ after it has been sutured and the isolation instrument removed therefrom.

After the opening O has been sealed the balloons 208 and 210 are deflated, as shown in FIG. 33. The exclusion instrument can then be withdrawn, i.e., slid proximally along the guidewire 206 until removed, then the guide wire can be removed, leaving the artery in its repaired state, as shown in FIG. 34. The relatively small diameter entry point P can be closed with manual pressure, a suture, or any type of puncture closure device, such as those disclosed in U.S. Pat. Nos.: 4,744,364, 4,852,568, 5,021,059, 5,061,274, 5,222,974, 5,282,827, 5,441,517, and 5,662,681, all assigned to the same assignee as this invention, and whose disclosures are incorporated by reference herein.

As should be appreciated from the foregoing the subject invention enables the easy and safe anastomosis of vessels, ducts, lumens or hollow organs by creating a fluid-exclusion zone through which blood or other fluid is precluded from flowing during the anastomosis. With some of the instruments, fluid flow can be accomplished around the fluid-exclusion zone, while fluid flow through that zone is precluded. In fact, as discussed above, the fluid-exclusion zone can be utilized for procedures on the wall of a vessel, duct, lumen or hollow organ which do not involve an anastomosis, so long as it is desirable to provide a space within the vessel, duct, lumen or hollow organ through which fluid is temporarily precluded from flowing.

Without further elaboration the foregoing will so fully illustrate our invention that others may, by applying current or future knowledge, adopt the same for use under various conditions of service.

We claim:

1. A system for forming an anastomosis junction of a first vessel, duct, lumen or hollow organ to a native vessel, duct, lumen or hollow organ of a living being at an anastomosis site, the site having an opening formed in the native vessel, duct, lumen or hollow organ, said system comprising an anastomosis connector and a fluid exclusion device, said anastomosis connector being arranged for securement to the native vessel, duct, lumen or hollow organ and to the first vessel, duct, lumen hollow organ so that they are in fluid communication with each other, said fluid exclusion device being arranged for insertion within the body of the being to a location in close proximity to the anastomosis site and being arranged to operate to form an exclusion zone within the native vessel, duct, lumen or hollow organ contiguous with the opening in the wall of the native vessel, duct, lumen or hollow organ at the anastomosis site through which fluid is temporarily precluded from flowing to thereby facilitate the formation of the anastomosis junction, said anastomosis connector comprising a resorbable tubular member, said anastomosis connector being arranged to be inserted through the opening in the wall of the native vessel, duct, lumen or hollow organ into the exclusion zone, said tubular member having a first portion in communication with the exclusion zone and a second portion arranged to extend through the opening in the wall of the native vessel, duct, lumen or hollow organ to enable the first vessel, duct, lumen or hollow organ to be connected thereto to complete the anastomosis junction.

2. The system of claim 1 wherein said fluid exclusion device enables fluid to flow from a location in the native vessel, duct, lumen or hollow organ upstream of the anastomosis site to a location in the native vessel, duct, lumen or hollow organ downstream of the anastomosis site while said fluid exclusion device is precluding fluid from flowing in the exclusion zone.

3. The system of claim 1 wherein said fluid exclusion device is operative to temporarily preclude fluid from flowing through said exclusion zone to facilitate the formation of the anastomosis junction.

4. The system of claim 3 wherein said fluid exclusion device enables fluid to flow from a location in the native vessel, duct, lumen or hollow organ upstream of the anastomosis site to a location in the native vessel, duct, lumen or hollow organ downstream of the anastomosis site, while said fluid exclusion device is temporarily precluding fluid from flowing in the zone.

5. The system of claim 2 wherein said fluid exclusion device comprises an elongated member having a passageway extending at least partially therethrough, an upstream blocking member and a downstream blocking member, at least a portion of said passageway being arranged to be located within the interior of the native vessel, duct, lumen or hollow organ, said upstream blocking member being arranged to be expanded to engage the interior of the native vessel, duct, lumen or hollow organ upstream of the anastomosis site to block the flow of fluid therebeyond, said downstream blocking member being arranged to be expanded to engage the interior of the native vessel, duct, lumen or hollow organ downstream of the anastomosis site to block the flow of fluid therebeyond, said passageway enabling fluid to flow from a location within the native vessel, duct, lumen or hollow organ upstream of said upstream blocking member to a location within the native vessel, duct, lumen or hollow organ downstream of said downstream blocking member.

6. The system of claim 5 wherein each of said expandable blocking members comprises an inflatable balloon.

7. The system of claim 2 wherein said fluid exclusion device comprises an elongated member having a passageway extending at least partially therethrough, an upstream blocking member and a downstream blocking member, said passageway being arranged to be located within the interior of the native vessel, duct, lumen or hollow organ, said upstream blocking member being arranged to constrict the native vessel, duct, lumen or hollow organ upstream of the anastomosis site to block the flow of fluid therebeyond, said downstream blocking member being arranged to constrict the native vessel, duct, lumen or hollow organ downstream of the anastomosis site to block the flow of fluid therebeyond, said passageway enabling fluid to flow from a location within the native vessel, duct, lumen or hollow organ upstream of said upstream blocking member to a location within the native vessel, duct, lumen or hollow organ downstream of said downstream blocking member.

8. The system of claim 7 wherein said elongated member comprises an over-the-wire dilator.

9. The system of claim 1 wherein said fluid exclusion device comprises a member for collapsing at least a portion of the native vessel, duct, lumen or hollow organ upstream of the anastomosis site and a member for collapsing at least a portion of the native vessel, duct, lumen or hollow organ downstream of the anastomosis site.

10. The system of claim 1 wherein said fluid flow preclusion means comprises means for cross clamping the native vessel, duct, lumen or hollow organ contiguous with the anastomosis site.

11. The system of claim 1 additionally comprising a stabilizer for stabilizing said fluid exclusion device with respect to the native vessel, duct, lumen or hollow organ.

12. The system of claim 11 wherein said stabilizer is arranged to apply suction to the exterior of the vessel, duct, lumen or hollow organ.

13. The system of claim 1 wherein said anastomosis device additionally comprises a retraction member coupled to said tubular member, said anastomosis device being arranged to be inserted through the opening into the exclusion zone, said tubular member having a portion arranged to be retracted out of the zone through the opening by said retraction member to serve as a point at which the bypass graft is connected.

14. The system of claim 1 wherein said fluid exclusion device is arranged to divert the flow of fluid around the exclusion zone during the securement of the anastomosis device.

* * * * *